United States Patent [19]
Lau

[11] Patent Number: 4,728,614
[45] Date of Patent: Mar. 1, 1988

[54] MUTANT HUMAN T CELL LINE PRODUCING IMMUNOSUPPRESSIVE FACTOR AND METHOD FOR OBTAINING SUCH MUTANTS

[75] Inventor: Catherine Y. Lau, Unionville, Canada

[73] Assignee: Ortho Pharmaceutical, Don Mills, Canada

[21] Appl. No.: 586,515

[22] Filed: Mar. 5, 1984

Related U.S. Application Data

[63] Continuation-in-part of Ser. No. 495,908, May 18, 1983, abandoned, and a continuation-in-part of Ser. No. 534,526, Sep. 21, 1983, abandoned.

[51] Int. Cl.$^4$ ........................ C12N 5/00; C12N 15/00; A61K 37/02; C12R 1/91

[52] U.S. Cl. ................................ 435/240.2; 530/351; 435/68; 435/172.1; 435/948

[58] Field of Search ...................... 435/68, 172.1, 240, 435/948; 260/112 R; 530/351

[56] References Cited

U.S. PATENT DOCUMENTS 4,239,498 12/1980 Rule ..................................... 424/88
4,544,632 10/1985 Yamamura et al. ............. 435/172.1

OTHER PUBLICATIONS

Murakami et al, "Establishment of Human T-Cell Hybridomas Secreting Non-Specific Suppressor Factors", Clinical Research, 31(4), p. 734A (11-1983).

Durand et al, "Mutant Human T Cell Line Constitutively Secreting High Titered Suppressor Factor(s)", Federation Proceedings, 41(3), p. 479 (1982), Abst. #1220.

Uytdehaag et al, "T-T Interactions in the Induction of Antigen Specific Human Suppressor T Lymphocytes in Vitro", Journal of Immunology, 123(2), pp. 646-653 (1979).

Belmont et al, "Physiology of Mixed Leukocyte Reaction Suppressor Factor", Journal of Immunology, 122(3), pp. 1022-1028 (1979).

Rich et al, "Regulatory Mechanisms in Cell Mediated Immune Responses", Journal of Experimental Medicine, 149, pp. 114-126 (1979).

Kapp et al, "Suppression of Antibody and T Cell Proliferative Responses to L-Glutamic Acid, L-Alanine, L-Tyrosine by a T Cell Factor", Journal of Experimental Medicine, 152, pp. 235-240 (1980).

Truitt et al, "Interaction Between T Cells and Non-T Cells in Suppression of Cytotoxic Lymphocyte Responses", Journal of Immunology, 123(2), pp. 745-750 (1979).

David H. Vesole et al., The Journal of Immunology, vol. 123, pp. 1322-1328 (1979).

Warner C. Greene et al., The Journal of Immunology, vol. 129, pp. 1986-1992 (1982).

E. M. Hersh et al., Clin. Exp. Immunol., 17, pp. 463-473 (1974).

John J. Farrar et al., The Journal of Immunology, vol. 125, pp. 2555-2558 (1980).

Steven Gillis et al., J. Exp. Med, The Rockefeller University Press, vol. 152, pp. 1709-1719 (1980).

H. William Schnaper et al., The Journal of Immunology, vol. 132, pp. 2429-2435 (1984).

Ellis H. Reinherz, JAMA, vol. 249, No. 13, pp. 1687-1689 (1983).

Michael Blaese, JAMA, vol. 251, No. 15, pp. 1935-1936 (1984).

A. H. Filipovich et al., The Lancet, pp. 470-475 (1984).

(List continued on next page.)

*Primary Examiner*—John E. Tarcza
*Attorney, Agent, or Firm*—David J. Levy; Richard J. Grochala; Geoffrey G. Dellenbaugh

[57] ABSTRACT

A stable mutant human T cell line is disclosed which secretes a high titer suppressor inducer factor. This suppressor inducer factor in turn induces production of a T cell suppressor factor which suppressed mitogen-induced T cell proliferation at high dilution. Also disclosed is a general method for mutating lymphoblastoid cell lines to yield mutants secreting enhanced levels of lymphokines.

24 Claims, 17 Drawing Figures

OTHER PUBLICATIONS

Friedrich Hasler et al., The Journal of Immunology, vol. 131, pp. 768–772 (1983).

"Generation of Functional Human T Cell Hybrids", J. Exp. Med., Irigoyen et al., vol. 154, pp. 1827–1837, Dec. 1981.

"An Inhibitor of DNA Synthesis Produced by Established Lymphoid Cell Lines", Clinical Immunology and Immunopathology, Vesole et al., vol. 14, pp. 489–501, 1979.

"Impaired Release of a T-Cell Specific Suppressor . . . ", Clin. Exp. Immunol., C. Lau et al. (1985), 61, pp. 489–495.

"Graft-Versus-Host Disease in Murine Bone Marrow . . . ", Gorczynski et al., Immuno. Ltrs., 11 (1985), pp. 293–299.

"Purification and Characterization of a Suppressor Activating Factor", Lau et al., 6th Int'l Congress of Immunology, Abstracts, 3.53.6, p. 448, 1986.

"Suppressor Activating Factor (SAF) . . . ", Messino et al., 6th Int'l Congress of Immunology, Abstracts, 6.13.21, 1986.

MUTANT HUMAN T CELL LINE PRODUCING IMMUNOSUPPRESSIVE FACTOR AND METHOD FOR OBTAINING SUCH MUTANTS

This application is a continuation-in-part of U.S. Ser. No. 495,908, filed May 18, 1983 and of U.S. Ser. No. 534,526, filed Sept. 21, 1983, both now abandoned.

FIELD OF THE INVENTION

This invention relates generally to new mutant cell lines and methods for producing them, and more specifically to a mutant human T cell line and its subclones which secrete high titer suppressive factor.

BACKGROUND

It is well established that activated lymphoid cells elaborate a variety of soluble factors (called "lymphokines") participating in the regulation of the immune response [reviewed by Altman et al. (1)]. The profile of factors reported include migration inhibitory factor (2,3), lymphotoxin (4,5), transfer factor (6,7), lymphocyte proliferation inhibitory factor (8,9) and interferon (10,11). Despite the overwhelming number of published studies on lymphokines with immunoregulating activities, the function-structural relationship of these molecules is still poorly understood.

Progress in the study of lymphokines has been strongly impeded by two major limitations. Firstly, due to the heterogenicity of the cell populations used to prepare conventional lymphokines, it is extremely difficult to assign a given biological activity to a distinct molecule. Secondly, the amounts of a given lymphokine in conventional preparations are usually too small to allow a precise biochemical analysis of the biologically active molecules. Moreover, since lymphocytes have a finite and usually short lifetime in culture, it is impossible to obtain repeatedly homogenous lymphokine preparations for characterization studies. These difficulties with regard to the study of lymphokines have caused workers in the field to experiment with cell lines and hybridomas.

The establishment of stable T cell lines secreting homogenous and distinct lymphokines has generated a large amount of information on the functions of soluble mediators [review by Moller (12)]. The continuous requirement for T cell growth factor (TCGF) for maintaining these clones has however hampered large-scale production of specific lymphokines. Recently, T-T hybridomas have been constructed (13–17) to immortalize lymphokine-secreting T cells. Since hybridomas are TCGF independent, some investigators in the field have thought they would serve as better sources than cloned T cell lines for preparing larger quantities of lymphokines for biochemical characterization.

Human lymphoid cell lines also produce a number of factors similar to mediators of cellular immunity released by lymphocytes. Gillis, et al., (18) showed that the human T cell lines Jurkat produces large quantities of human interleukin 2 (IL2) upon stimulation with mitogen. Farrar, et al., (19) showed that the mouse thymoma EL4 secretes high concentrations of mouse IL2 upon stimulation by the mutagen phorbol myristate acetate. These two cell lines produce such abundant quantities of the respective factors that detailed biochemical analysis of their function-structural relationships are underway.

Vesole, et al., (20) have described previous reports of lymphoid lines which secrete low levels of uncharacterized suppressor factors that inhibit DNA synthesis of mitogen stimulated lymphocytes, while noting that stimulation of lymphocyte growth (and thus of DNA synthesis) may also be caused by supernatants of lymphoid cell lines. In the Vesole reference itself, the authors indicate that the human lymphoid cell line CCRF-CEM ("CEM") secretes a substance which by itself increases DNA synthesis in lymphocytes. These authors also disclose that CEM secretes an uncharacterized substance which weakly inhibits mitogenic response in mononuclear cells stimulated with a mitogen such as PHA. From FIG. 1 in this reference, it can be seen that 50% inhibition of the mitogenic response is achieved at a dilution of about six-fold (i.e., about $10^{-0.8}$). This inhibiting substance is stated to elute on a Sephadex G-100 column with the albumin peak and thus has a molecular weight of about 70,000 dalton.

One of the references cited in Vesole (Yoshida, et al., J. Immunol., 117, 518 (1976)) also discloses work with CEM (among other cell lines) to examine its ability to release lymphokines into its culture medium, but there is no disclosure of any T cell suppressor factor being looked for or found.

Although various other mutants of various cell lines (including CEM) have been produced by other investigators, none of them even suggested that one could obtain a cell line secreting high titer suppressor factor.

Reference is made in this regard to Foung, et al., PNAS (U.S.A.), 79: 7484–7488 (December 1982), Lakow, et al., J. Immunol., 130, 169–172 (January 1983), and DeFreitas, et al. (16), who reported work with the human T cell line Jurkat.

Additionally, several authors have reported work with mutants of the T cell line CEM. Okada, et al., PNAS (U.S.A.) 78: 7717–7721 (December 1981), reported work with an 8-azaguanine-resistant mutant of CEM, while Irigoyen, et al., (17) reported establishment of a 6-thioguanine-resistant mutant from the cell line CEM.

Irigoyen, et al., describe the preparation of a 6-thioguanine (6T) resistant mutant of the CEM cell line and the subsequent fusing of this mutant with lectin-stimulated human T cells to produce human-human T cell hybridomas. No mention is made of the source of the parent CEM cell line. The method used for production of the mutant involved an initial mutation by ethyl methanesulfonate followed by exposure to increasing concentrations of 6T (1.25 μg–5 μg/ml), after which the mutant cells were maintained in 16.7 μg/ml of 6-thioguanine.

Irigoyen, et al., is the only group known to Applicant which has reported on the characteristics of a 6T-resistant mutant CEM line. Their mutant line CEM-T15 (the only one discussed in the reference) was described as lacking the OKT3 antigen and having a chromosome number (karotype) of 35–47, the same as the parent CEM line used in its production. Additionally, Irigoyen's parent CEM line and the mutant line CEM-T15 both grew normally in the presence of $10^{-8}$M aminopterin (0.04 μg/ml), both died in the presence of $10^{-7}$M aminopterin (0.04 μg/ml), and there was differential growth (CEM grew, while CEM-T15 died) at $3.3\times10^{-8}$M and $6.6\times10^{-8}$M aminopterin (0.013 and 0.026 μg/ml, respectively). The reference also indicates that CEM-T15 . . . "inhibits the background level of PFC (plaque forming cells) generated in cultures containing B cells and PWM (pokeweed mitogen)." This result indicates that CEM-T15 inhibits B cell differentiation. No information is given regarding any action on T cell differentiation.

These reports provided no suggestion that one could produce a stable mutant cell line which would have excellent growth characteristics and would secrete high titer suppressor factor. In fact, the present inventor observed in the course of the work leading to this invention that an azaguanine-resistant mutant CEM line was produced which showed deficiency in the enzyme hypoxanthine guanine ribotransferase (like the 6T-resistant mutant) but did not exhibit the beneficial characteristics found in the cell line of the present invention.

SUMMARY OF THE INVENTION

The present Applicant has now discovered a novel stable 6-thioguanine resistant mutant of the lymphoblastoid cell line CCRF-CEM (designated 6T-CEM) which secretes constitutively into the growth medium a high titer of a non-mitogenic, non-cytotoxic T cell suppressor-inducer factor (SIF) which induces production of a T cell suppressor factor (TSF). These factors were unknown prior to the present invention. This discovery is most surprising in view of the results reported by Vesole, et al., and Irigoyen, et al.

The cell-free supernatant of this novel mutant (containing SIF) suppresses at least 90% of mitogen-induced T cell proliferation at dilutions as high as $10^{-6}$, while the cell-free supernatant of its most productive subclone exhibits such suppression at a dilution up to $10^{-9}$. The supernatants do not suppress mitogen-induced B cell proliferation at these dilutions. This titer has remained constant for over 8 months. The mechanism of action, the cellular target, and the biochemical characterization of the factors responsible for the observed suppression have been determined. The factor SIF also exhibits T cell proliferation suppression in vivo.

The term "stable" as used herein in reference to the subject mutuant and its subclones means that the mutant and its subclones continue to secrete high titer SIF for at least six months. Additionally, the "stable" mutant and subclones do not suffer any appreciable change in their karyotype over the same period. It should be understood in general that mutants or subclones of mutants which are not stable are not practically useful, since they will not serve as reliable sources of lymphokines in general or SIF in particular.

The term "non-mitogenic" as used herein means that the SIF secreted by the subject mutant and its subclones has no observed mitogenic effect on human T cells. The term "non cytotoxic" as used herein means that the SIF secreted by the subject mutant and its subclones has no observed cytotoxic effect on human T cells. The term "suppression" and its variants as used herein mean a diminution in the activity which is "suppressed", which diminution may be partial or complete.

This mutant cell line is useful not only for its secretion of suppressor-inducer factor, but also as a potential partner in hybridoma formation. With regard to this second utility, aminopterin sensitivity is extremely important, because human lymphocytes (and thus human hybridomas produced from human lymphocytes) are much more sensitive to aminopterin than corresponding mouse lymphocytes or hybridomas. Accordingly, in order to differentially select human hybridomas using HAT medium, smaller amounts of aminopterin must be used in the medium to ensure survival of the desired hybridomas and hence the unfused cell line must be very sensitive to the material.

The SIF and TSF produced as part of the subject invention are useful for suppressing T cell proliferation both in vitro and in vivo.

Included within the present invention are the subject mutant cell line 6T-CEM, subclones of this mutant cell line (including that designated 6T-CEM-20), methods for preparing the cell line and the subclones, the suppressor inducer factor produced by the mutant cell line and its subclones, the T cell suppressor factor induced thereby, and methods for suppressing T cell proliferation using said factors (both in vitro and in vivo). These methods comprise treating said T cells with (in vitro), or administering to an animal in need of suppression of T cell proliferation (in vivo), an effective T cell proliferation suppressing amount of either the suppressor inducer factor or the T cell suppressor factor. The present invention also includes a method of mutating any lymphoblastoid cell line (of T cell or B cell origin) to yield a mutant cell line producing enhanced levels of lymphokines.

The subject mutant cell line 6T-CEM was produced by treating the parent line CEM (obtained from the American Type Culture Collection) with an initial high concentration of 6T (about 20–30 μg/ml of 6T) for a period of time sufficient to kill at least 90% of the cells; the small percentage of surviving cells after seven days treatment with 30 μg/ml of 6T constituted the mutant cell line 6T-CEM. In contrast to the prior art, no additional mutagen was used and the cells were exposed to an initial high concentration of 6T rather than progressively increasing concentrations. It appears that the treatment of the parent line with a high concentration of 6T from the beginning was significant in yielding the subject mutant cell line. Prior art references dealing with mutating procedures have taught one to begin with low concentrations of mutating agent and progressively increase the amount. The Irigoyen, et al., reference is typical.

Once the subject cell line was obtained, it was possible by techniques known in the art to subclone the subject mutant cell line to obtain subclones having higher levels of suppressor-inducer factor production. Both the subject mutant cell line and its subclones possess the OKT3 antigen and may be detected with OKT3 monoclonal antibody.

The discovery of this SIF-secreting mutant cell line is surprising not only in view of the state of the art, but also in view of applicant's unsuccessful attempts to produce such a mutant cell line of CEM using azaguanine. The parenteral line CEM secretes only low levels of an uncharacterized suppressive factor, as set out in Vesole, et al. The Okada, et al., reference noted above, which discloses an azaguanine-resistant mutant of CEM, indicates only that T-T hybridomas prepared using this cell line secreted IL-2 and a helper factor. No information is presented regarding any factors which might be secreted by the azaguanine-resistant mutant CEM itself. Moreover, Okada et al., indicate in the right hand column on page 7720 that "it may be impossible to find T leukemic cell lines that produce several other lymphokines such as killer helper factor(s) or T-cell replacing factor". This observation teaches away from the subject invention.

Because of the difficulties in purifying factors which occur only in low concentration, the prior art low titer suppressive factors are as a practical matter impossible to purify and characterize. Typically, 50-90% of any protein is lost in the purifying steps. Hence, if one were to attempt to purify prior art factors (such as that of Vesole, et al.), activity would vanish before purification was achieved.

The present Applicant has also discovered that the method used above for producing the mutant cell line 6T-CEM is also effective to produce stable mutants of other lymphoblastoid cell lines which have enhanced production of lymphokines over the parent cell line used for production of the mutant. For example, the lymphoblastoid cell line HSB (ATCC CCL 120.1) produces an uncharacterized suppressive factor which suppresses mitogen-induced T cell differentiation only at a dilution of $10^{-1}$. The stable mutant cell line 6T-HSB produced by the same method as 6T-CEM, by comparison, produces a factor that suppresses such proliferation at a dilution of $10^{-4}$.

The present invention therefore includes a method for mutating a parent lymphoblastoid cell line to yield a stable mutant cell line secreting an enhanced level of lymphokine which comprises treating said parent lymphoblastoid cell line with from about 20 to about 30 microgram/ml of 6T for a period of time sufficient to kill at least 90% of the parent cells, and thereafter isolating the viable cells. This method is applicable to lymphoblastoid cell lines of human or animal origin, as well as to lymphoblastoid cell lines of T cell or B cell origin.

The preparation and characterization of the subject mutant cell line and the resulting suppressor-inducer factor and the T cell suppressor factor induced thereby will be better understood by reference to the following description and examples.

$$1 - \frac{\text{cpm of cultures treated with column fraction}}{\text{cpm of cultures treated with eluting buffer}} \times 100$$

Figure 11:
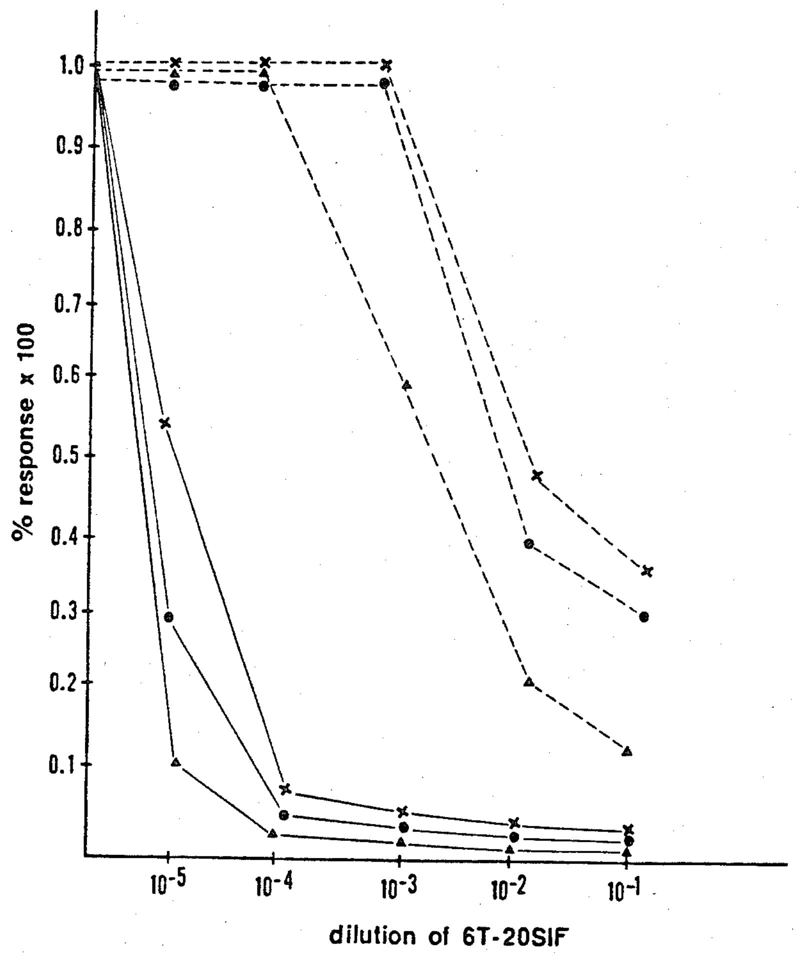

FIG. 11. Effect of 6T-20SIF treated T lymphocytes in suppressing the proliferation of allogeneic T lymphocytes to mitogenic stimulation. T lymphocytes were exposed to various dilutions of 6T-20SIF or medium for 24 hours and then set up in coculture assay with $5\times10^4$ fresh, allogenic T cells in the presence of 0.1% PHA (———) or with $10^5$ B and $5\times10^4$ T cells in the presence of 1/64 dilution of PWM (---). Dilutions of precultured T lymphocytes used were $10^4$ (×), $2.5\times10^4$ (●), and $5\times10^4$ (Δ). $^3$H-thymidine uptake was measured 4 days later. The $^3$H thymidine uptake for $5\times10^4$T cells alone in 0.1% PHA is 12611±532 cpm.

The $^3$H-thymidine uptake for $10^5$ B cells and $2.5\times10^4$ T cells in 1/64 dilution of PWM is 7214±650 cpm.

Figure 12:
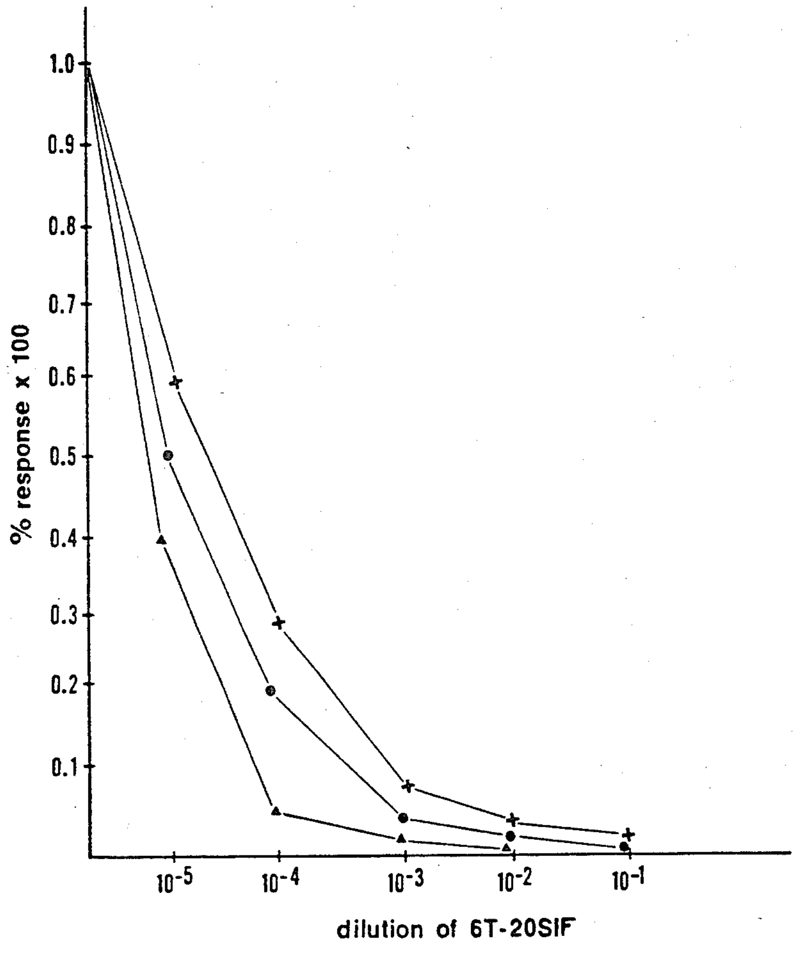

FIG. 12. Effect of 6T-20SIF treated T lymphocytes in suppressing allogeneic T lymphocytes in a one-way MLC assay. T lymphocytes were exposed to various dilutions of 6T-20SIF or growth medium for 24 hours and then set up in a coculture assay with $5\times10^4$ fresh T cells in a one way MLC reaction stimulated by $10^4$ mit-C treated CCRF-SB cells. Dilutions of precultured T cells used were $10^4$ (×), $2.5\times10^4$ (●), and $5\times10^4$ (Δ). $^3$H-thymidine uptake was measured 5 days later. $^3$H-thymidine uptake in a standard MLC assay without added supernatant is 13326±216 cpm.

Figure 13:
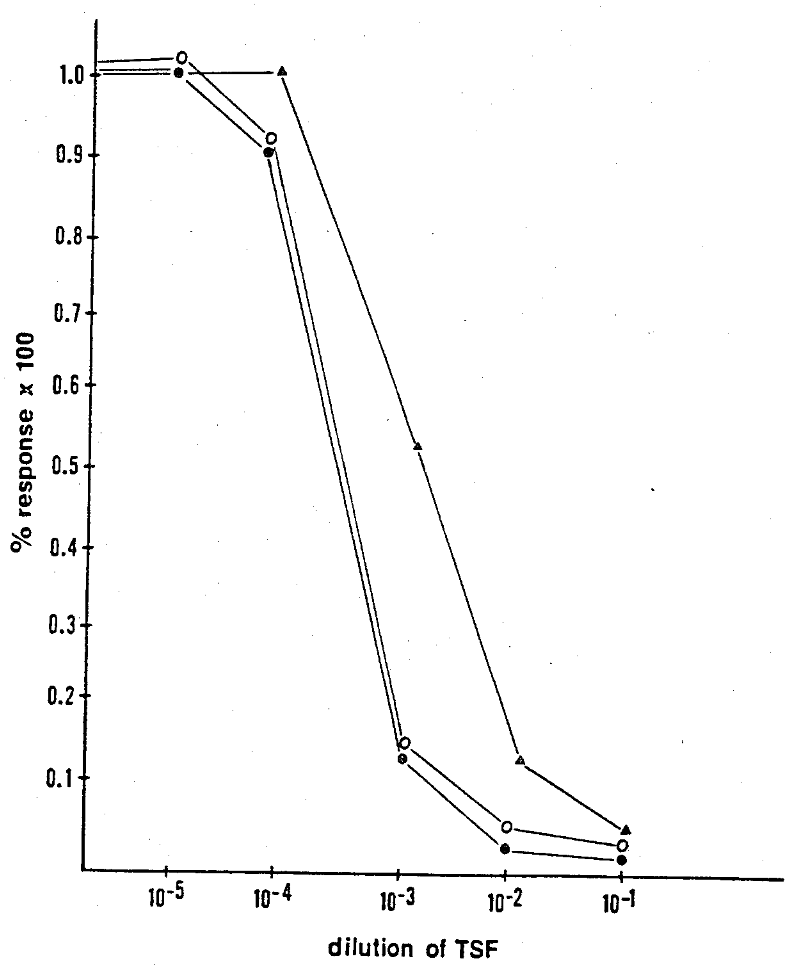

FIG. 13. Production of T cell suppressor factor (TSF) by 6T-20SIF treated lymphocytes. T-lymphocytes were incubated at $3\times10^6$ cells/well with 1/500 dilution of 6T-20SIF for 24 hours, washed, and set up at $10^6$ cells/ml in RPMI+2% FCS. Supernatants were collected at 24 hours (Δ), 48 hours (o), or 72 hours (●) after culture initiation. Various dilutions of supernatants (TSF) were set up in a PHA induced T cell proliferation assay.

Figure 14:
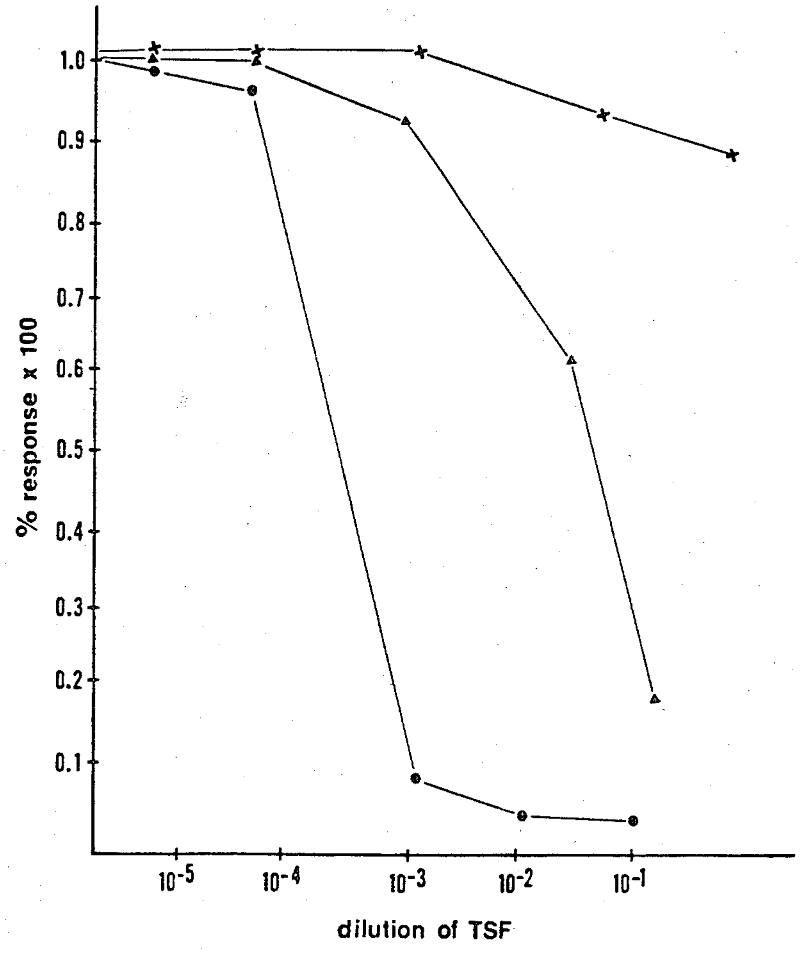

FIG. 14. Suppressive effects of TSF. Various dilutions of TSF (as indicated in the figure) were added to cultures of $10^5$ T lymphocytes (●) stimulated with 0.1% PHA (20216±2162 cpm) or $2\times10^4$ T lymphocytes, $10^5$ B lymphocytes (Δ) stimulated with 1/64 dilution of PWM (942102±2116 cpm) or $10^5$ B lymphocytes (x) stimulated with 1/64 dilution of PWM (625±25). The % response is expressed as a ratio of $^3$H-thymidine uptake by cells treated with TSF to cells treated with medium. The actual $^3$H-thymidine uptake in cpm for each group in the absence of TSF was indicated in the parentheses.

Figure 15:
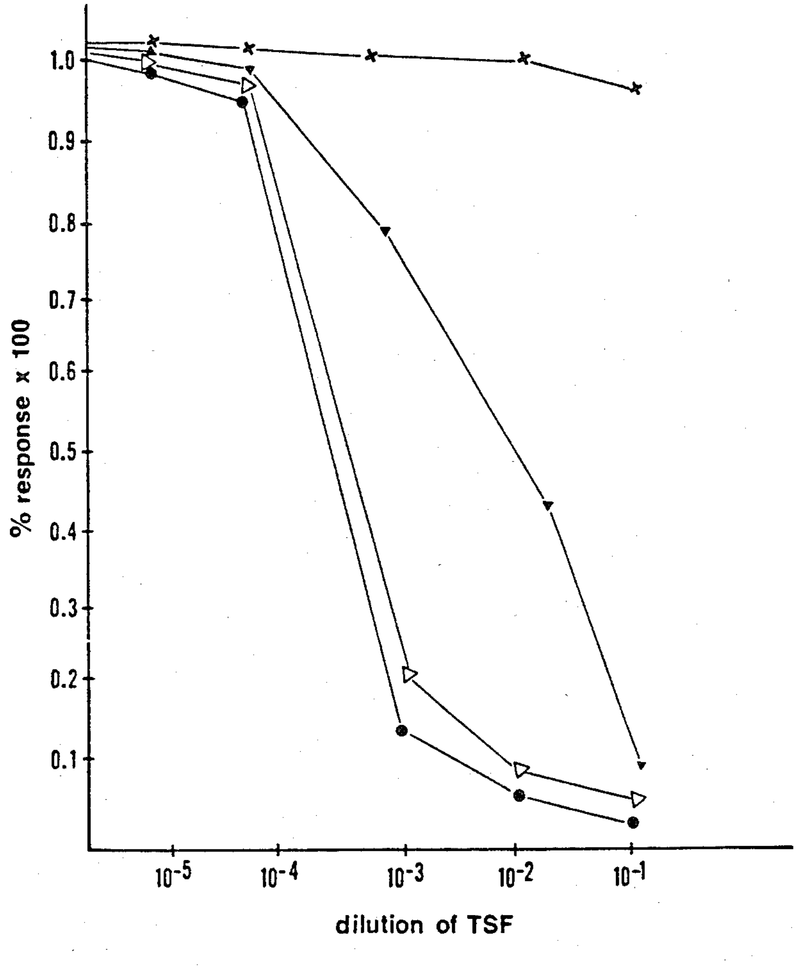

FIG. 15. Time course of TSF induced suppression. Various dilutions of TSF were added to a PHA induced T cell proliferation assay at day 0 (●), day 2 (Δ) or day 4 (×) just before $^3$H-thymidine addition. $^3$H-thymidine uptake by T lymphocyte alone in the presence of PHA is 12112±123 cpm. $^3$H-thymidine uptake was also measured at 3 days after culture initiation (Δ) with TSF added at the beginning of the culture period. The $^3$H-thymidine uptake of T cells alone in the presence of PHA in a 3 day assay is 10216±123 cpm.

Figure 16:
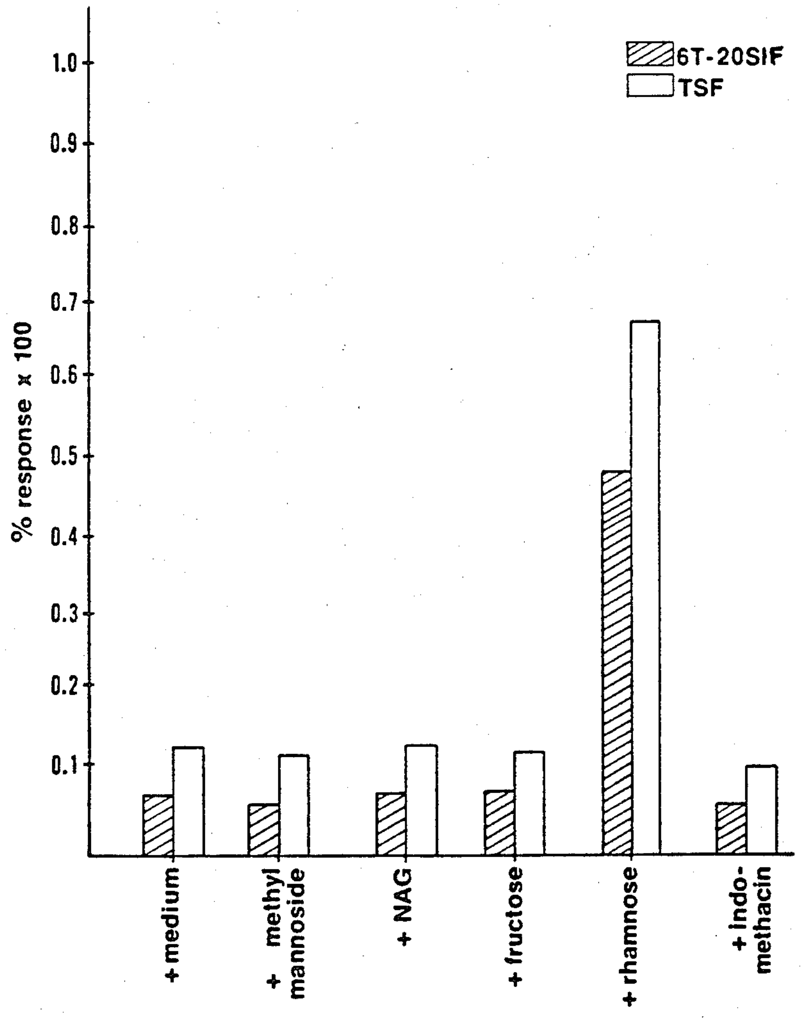

FIG. 16. Effect of monosaccharides and indomethacin on the suppressive activities of 6T-20SIF and TSF. T lymphocytes were stimulated with 0.1% PHA in the presence of $10^{-5}$ dilution of 6T-20SIF or $10^{-3}$ dilution of TSF together with 50 mM of α-methyl mannoside, NAG, fructose, or rhamnose, or 10 μg of indomethacin. $^3$H-thymidine uptake was measured on day 4 and % response was calculated.

Figure 17:
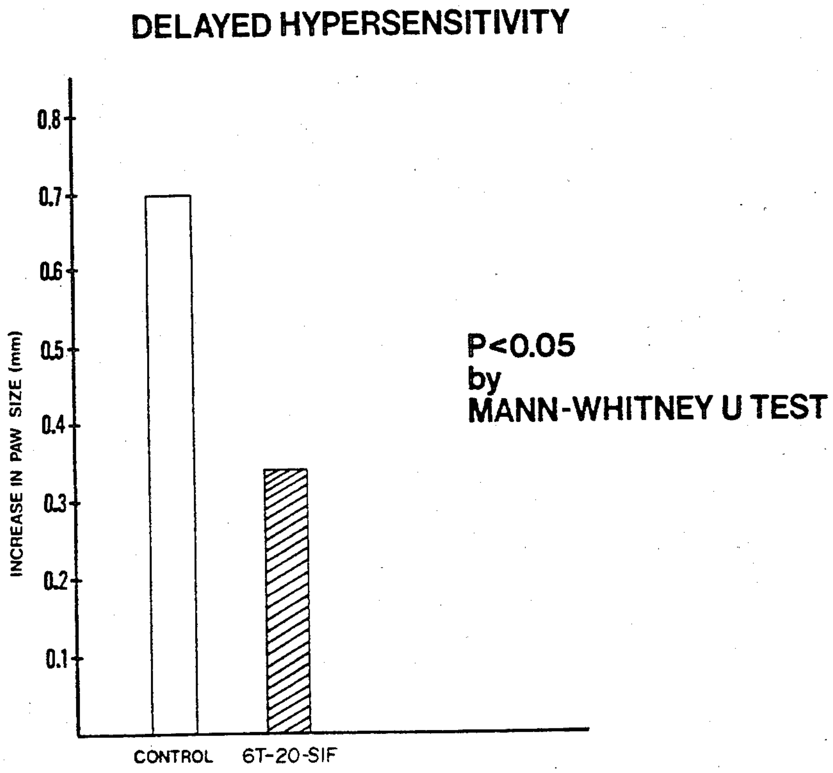

FIG. 17. Effect of 6T-20SIF in delayed-type hypersensitivity. C3H male mice were dosed with 6T-20SIF in the left foot pad on day 4 and 5 after immunizations. The mice were challenged on day 5 and foot pad measurements were made 24 hours later.

DETAILED DESCRIPTION OF THE INVENTION

The following materials were used in the Examples. Purified phytohemagglutinin (PHA-P) was obtained from Wellcome. Pokeweed mitogen (PWM) was obtained from Gibco. Aminopterin and mitomycin C (mit-C) were obtained from Sigma. C57/B6 and DBA/2 mice were obtained from the Jackson Laboratory. Growth medium for human cell lines consisted of α-minimum essential medium (α-MEM) (Gibco) supplemented with penicillin (Gibco, 50 μg/ml), streptomycin (Gibco, 100 μg/ml), L-glutamine (Gibco, 2.0 mM) and 2-10% fetal calf serum (FCS, Gibco). The medium for the T cell proliferation assay was the same except RPMI 1640 (Gibco) was used instead of α-MEM; 10% FCS was used at all times. The monosaccharides fructose, NAG, rhamnose, and α-methyl mannoside, and the prostaglandin inhibitor indomethacin were obtained from Sigma.

EXAMPLE I

Generation of 6-thioguanine (6T) resistant mutant 6T-CEM and the subclone 6T-CEM-20.

The 6-thioguanine (2-amino-6-mercaptopurine; 6T) was obtained from Sigma (Cat. No. A-4882). 100 mg of 6T was dissolved in 100 ml of distilled water. 1 or 2 drops of 10N NaOH were added to help the 6T to dissolve completely. The pH of the final solution is about 9.

The lymphoblastic leukemic line CEM (CCRF-CEM, ATCC CCL 119) was obtained from the American Type Culture Collection, Rockville, MD, and was maintained in 90% α-MEM and 10% FCS. CEM cells at log phase ($10^6$ cells/well) were treated with various concentrations of 6T and viability was assayed 7 days later (Table 1). Cells treated with 30 μg/ml of 6T were selected for further studies. The remaining viable cells (4%) were grown in 25 mm culture flasks until a significant number of cells was observed, after which dead cells were removed by a Ficoll-Hypaque gradient. The viable cells were divided into 2 parts. One part was maintained in α-MEM+FCS with fresh medium added every third day and the cells were passaged every week. The other part was plated in 96 well microtiter plates for subcloning. The subclones grew up in about 2–3 weeks, after which they were transferred to 24 well Linbro trays. When the cells reached a density of $10^6$/well, they were tested for aminopterin sensitivity and the production of the suppressor inducer factor (Table 2). 6T-CEM-20, one of the subclones which showed the highest level of factor production, was selected for further studies.

The growth characteristics, karyotype, sensitivity to aminopterin, level of suppressor activity and effects of supernatants on other immunological assays are listed in Table 3 for CEM, 6T-CEM, 6T-CEM-20, and Az-CEM (an azaguanine-resistant CEM mutant).

The line 6T-CEM-20 has been showing a consistent level of suppressor inducer factor secretion for greater than eight months, indicating no loss of chromosome(s) involved in the secretion of the factor. The stability data are shown in Table 4.

EXAMPLE II

Production of suppressive supernatants.

6T-CEM cells were routinely maintained in α-MEM containing 10% FCS. For production of the suppressive supernatants from 6T-CEM, cells were washed and suspended at $2\times10^5$ cells/ml or $10^6$ cells/ml in α-MEM with 2% FCSs. Supernatant was harvested 48 hours later and the functional activities were assessed. The standard procedure for the production of the lymphocyte derived suppressor factor TSF involved incubation of the lymphocyte population of interest at $3\times10^6$ cells/ml in the presence of 1/500 dilution of 6T-20SIF (the suppressor-inducer factor produced by the subclone 6T-CEM-20). After 24 hours, cells were washed 3–4 times and then set up at $1\times10^6$ cells/ml in RPMI 1640 with 2% FCS. Supernatants were harvested 72 hours afterwards unless otherwise indicated.

EXAMPLE III

Preparation of purified populations of lymphocytes.

Peripheral blood lymphocytes (PBL) were obtained from the blood of nornal donors by using standard Ficoll-Hypaque gradient techniques (21). The T and non-T cells were separated by standard sheep red blood cell (SRBC) rosetting technique (21). Briefly, $5\times10^6$/ml PBL were incubated with 1% neuraminidase-treated SRBC, and rosetted cells were separated from non-rosetted cells on a Ficoll-Hypaque gradient. The rosetted cells were designated as T cells. Purified B lymphocytes were obtained from non-rosetted cells by removal of residual T cells using the Pan T monoclonal antibody OKT11 and complement. Purified OKT4+ and OKT8+ cells were obtained by treating T lymphocytes ($10^7$/ml) with 1 μg of the respective monoclonal antibody, followed by complement lysing. Dead cells were removed by Ficoll-Hypaque gradient and purity of the subset was assayed with the ORTHO Spectrum III cytofluorograph (Ortho Diagnostic Systems) using fluorescent labeled monoclonal antibodies. Adherent cells were removed by putting 10 ml of lymphocytes at $10^6$/ml on a 100 mm Petri dish (Falcon). Cells were incubated at 37° C. for 2–3 hours. The nonadherent cells were recovered from the medium and the subsequent washes with gentle pipetting. Adherent cells were released from the plate by the addition of ethylenediamine tetraacetic acid (EDTA, 0.2 mM, Gibco). Employing these techniques, T lymphocytes were usually 95% OKT11+ and 1–2% OKM1+ before removal of adherent cells, and 96% OKT11+ and OKM1− removal of adherent cells. B cells were OKT11−, 68% Ig+ and 20% OKM1+ before removal of adherent cells, and 78% Ig+ and 2% OKM1+ after removal of adherent cells. OKT11 staining was done by direct fluorescent technique using FITC-conjugated monoclonal antibody. Ig staining was done by using FITC-conjugated goat anti-human Ig (Meloy), and OKM1 staining was done by indirect fluorescent staining technique using OKM1 and FITC-conjugated goat anti-mouse Ig (Meloy). All OK monoclonal antibodies were supplied by Ortho Diagnostic Systems.

EXAMPLE IV

Lymphocyte proliferation.

T cell proliferation: $7\times10^4-10^5$ human T lymphocytes were cultured in U bottom microtiter plates (Flow) in the presence of 0.1% PHA-P or 1/64 PWM for 4 days. $^3$H thymidine (0.1 μCi/well) was added for the last 6 hours of the culture period. T cell dependent B cell proliferation: $2\times10^4$ T cells and $10^5$ B cells were cultured together in the presence of 1/64 dilution of PWM for 4 days. $^3$H thymidine was added for the last 6 hours of the culture period. B cell proliferation was carried out exactly the same manner with no T cells added to the culture. In all cases, cells were subsequently harvested onto filter paper using a multiple-channel automated cell harvester (Flow) and washed repeatedly with distilled water. Cell associated radioactivity was determined by scintillation counting in an automated counter. All of the results were expressed as % response calculated according to the formula:

$$\% \text{ response} = \frac{\text{cpm of supernatant treated-cultures}}{\text{cpm of control cultures}} \times 100$$

EXAMPLE V

Coculture experiments.

Lymphocytes were treated at $3\times10^6$ cells/ml with various dilutions of 6T-20SIF or growth medium for 24 hours. Cells were washed extensively (3 to 4 times) to remove residual 6T-20SIF, after which they were set up in coculture assays with allogenic T and B cells at various concentrations indicated in reference to FIGS. 11 and 12. In T cell proliferation assay, various concentrations of cultured cells were added to $5\times10^4$ fresh T cells in the presence of 0.1% PHA. In the T cell induced B cell proliferation assay, various concentrations of cultured cells were added to $2\times10^4$ T and $10^5$ B cells in the presence of 1/64 dilution of PWM. In the B cell proliferation assay, various concentrations of cultured cells were added to $10^5$ B cells in the presence of 1/64 dilution PWM. Cells were cultured for 4 days and $^3$H thymidine was added for the last 6 hours of the culture period. For one way mixed lymphocyte culture (MLC) experiments, various dilutions of cultured cells were added to $5\times10^4$ T lymphocytes stimulated with $10^4$ mit-C treated SB cells (a human lymphoblastoid cell line obtained from ATCC, 30 μg/ml of mit-C for 30 minutes). Cells were cultured for 5 days, $^3$H thymidine being added for the last 6 hours of the cultuare period. Cell harvesting was done as described above. The % response was calculated according to the formula:

$$\% \text{ response} = \frac{\text{cpm of cocultures containing 6T-20SIF treated cells}}{\text{cpm of cocultures containing corresponding number of medium treated cells}} \times 100$$

EXAMPLE VI

Mixed lymphocyte culture (MLC).

Human: $5\times10^4$ or $10^5$ human T lymphocytes were cultured with $10^5$ mit-C-treated (30 μg/ml per $10^7$ cells for 30 minutes at 37° C.) allogenic non-rosetted cells, autologous non-rosetted cells, or DBA spleen cells (xenogenic cells) for 5 days. $^3$H thymidine was added for the last 12 hours of the culture period. Mouse: $2\times10^5$ C57/B6 spleen cells were cultured with $2\times10^5$ mit-C-treated DBA spleen cells for 5 days and $^3$H thymidine was added for the last 12 hours of the culture period. Percent response was calculated according to the same formula used for lymphocyte proliferation assays. For the coculture assays, various dilutions of T lymphocytes pretreated with 6T-20SIF or medium were cocultured with $5\times10^4$ fresh T cells together with $10^4$ mit-C treated SB cells as stimulator cells. Cells were cultured for 5 days and $^3$H thymidine was added for the last 6 hours of the culture period.

EXAMPLE VII

Cytotoxic T cell assay.

Purified T lymphocytes were suspended at $10^6$/ml in RPMI containing 5% human AB serum. 100 μl of cells were put into U bottom microtiter wells together with $10^4$ mit-C treated SB cells (30 μg mit-C for 30 min.) and various dilutions of TSF. After 3 days, $10^4$ $^{51}$Cr labeled SB cells were added to each well and the plates were spun at 1000 g for 10 min. After 4 hours of incubation at 37°, 100 μl of supernatant was removed and counted in a Beckman Gamma counter. The % cytotoxicity was calculated using the following formula:

$$\% \text{ cyctotoxicity} = \frac{(^{51}\text{Cr released by } SB \text{ cell stimulated cultures}) - (^{51}\text{Cr released by unstimulated cultures})}{\text{Total } ^{51}\text{Cr released by lysed SB cells}} \times 100$$

EXAMPLE VIII

Acidification and alkalization.

The cell-free supernatant was acidified with 10N HCl or alkalized with 10N NaOH for 30 minutes and then returned to neutral pH. Controls were set up consisting of medium substituted for the HCl or NaOH.

Heat inactivation:

6T-20SIF was heat inactivated in a 56° C. water bath for 30 minutes.

Enzymatic digestion:

Trypsin was added to 6T-20SIF at a final concentration of 0.1% and incubated for 2 hours at 37° C. Enzymatic reaction was stopped by the addition of FCS to a final concentration of 10%. Controls were set up consisting of medium substituted for the trypsin.

Ammonium sulfate precipitation.

Cell-free supernatant was centrifuged at 10,000 rpm for 20 minutes to remove any debris. Ammonium sulfate was then added gradually to give a final 50% ammonium sulfate saturation. After stirring for 45 minutes, the solution was centrifuged at 10,000 rpm for 30 minutes. The precipitate, which contained the suppressor activity, was exhaustively dialyzed against PBS. All steps were carried out in the cold and the pH was maintained between pH 7.0 and pH 7.4.

Chromatography on Sephacryl®S-200 column.

The 50% ammonium sulfate fraction containing the suppressor activity was further purified on a Sephacryl®S-200 superfine column (2.5 cm×50 cm). The column was equilibrated with phosphate-buffered saline (PBS) and had a flow rate of 30 ml per hour. 2 ml of the dialyzed, 50% ammonium sulfate precipitated fraction was applied on the column. It was eluted with PBS and volumes of 5 ml were collected. The protein profile was followed by reading optical density at 280 nm.

Figure 1:
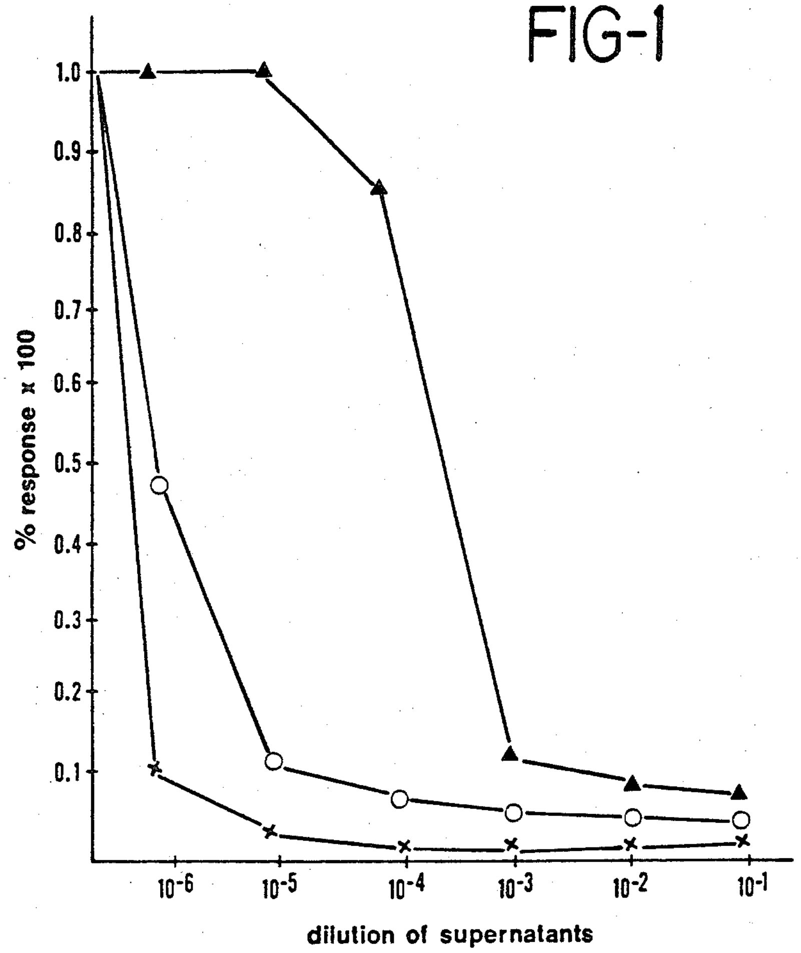
FIG. 1. Suppression of T cell proliferation by supernatants of CEM, 6T-CEM and its subclone 6T-CEM-20. $10^5$ cells/well of T lymphocytes were stimulated with 0.1% phytohemagglutinin (PHA). Cell free supernatants from CEM (Δ), 6T-CEM (o) and 6T-CEM-20 (×) were added at different dilutions as indicated in the figure. Proliferation was guantitated by measuring $^3$H-thymidine uptake on day 4. The $^3$H-thymidine uptake for T cells alone in PHA was 12021±1216 cpm.

Production of suppressive supernatants by CEM, 6T-CEM and its subclones (FIG. 1).

6T-CEM, the thioguanine resistant mutant of the lymphoblastoid cell line CEM, secretes into the growth medium a high titered suppressive factor which inhibits T cell proliferation to PHA to the 95% level (10/10 experiments). Applicant has discovered that the parenteral line CEM used herein also secretes a suppressor factor, but the titer of this factor is about 1000 fold lower than the titer of SIF produced by 6T-CEM. By subcloning 6T-CEM, there was obtained one clone 6T-CEM-20 which produced 10 fold higher suppressive activity than 6T-CEM (FIG. 1). 6T-CEM-20 has been showing stable levels of factor production for over 8 months. The supernatant of 6T-CEM-20 is referred to herein as 6T-20SIF. The suppressive activity (50% response) of 6T-20SIF has also been observed at a dilution of $10^{-9}$.

Figure 2:
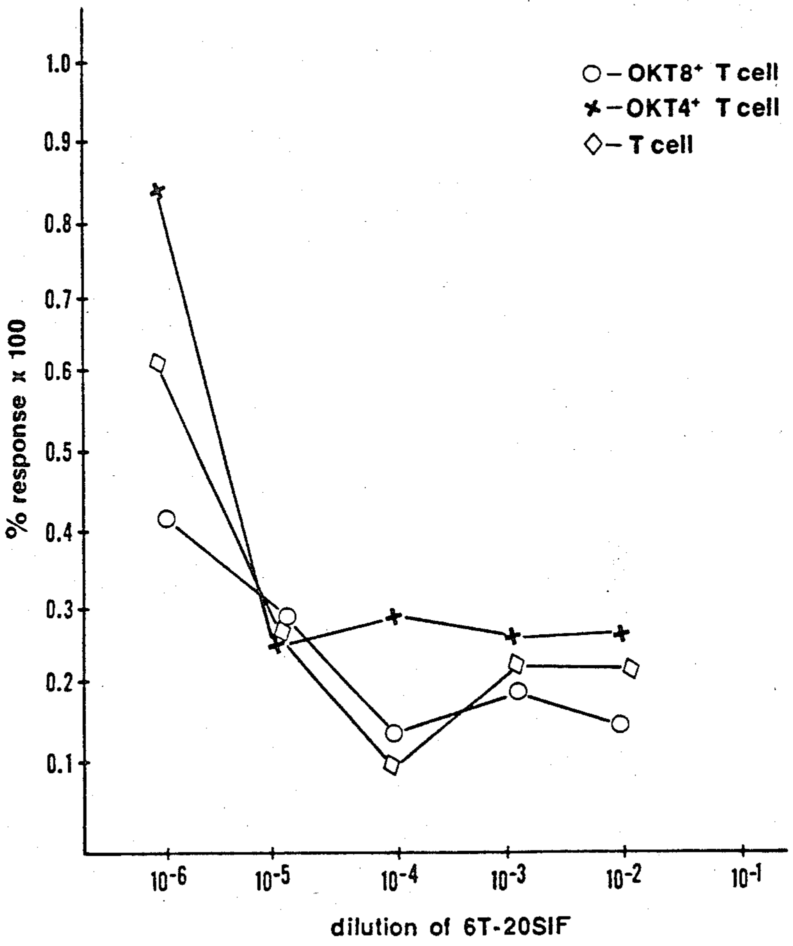
FIG. 2. Suppressive effect of 6T-20SIF (the SIF secreted by 6T-CEM-20) on different subsets of T cells. Unseparated (Δ), OKT4+ (×) or OKT8+ (o) populations were stimulated with PHA in the presence of various dilutions of 6T-20SIF. Proliferation was quantitated by measuring $^3$H-thymidine uptake on day 4. The $^3$H-thymidine uptake for respective populations alone in the presence of PHA were 29520±281 cpm, 27063±1344 cpm, and 24920±2637 cpm.

The effect of 6T-20SIF on different subsets of T cells (FIG. 2).

T cells were fractionated into OKT4+ and OKT8+ subpopulations by monoclonal antibody-mediated complement cytolysis. Dead cells were removed on a Ficoll-Hypaque gradient. The purified cells were 95% viable and showed 90–95% purity as tested by fluorescent antibody labelling and measured by the ORTHO Spectrum III cytoflorometer. The differential effects of 6T-20SIF on OKT4 (helper/inducer) and OKT8 (suppressor/cytotoxic) subsets are shown in FIG. 2. 6T-20SIF suppressed equally well the proliferation of both the OKT4+ and the OKT8+ populations.

6T-20SIF did not suppress via a cytotoxic mechanism. The number of cells staining positively in the presence of trypan blue did not increase when cultured 3–7 days without mitogen or alloanitigen.

Figure 3:
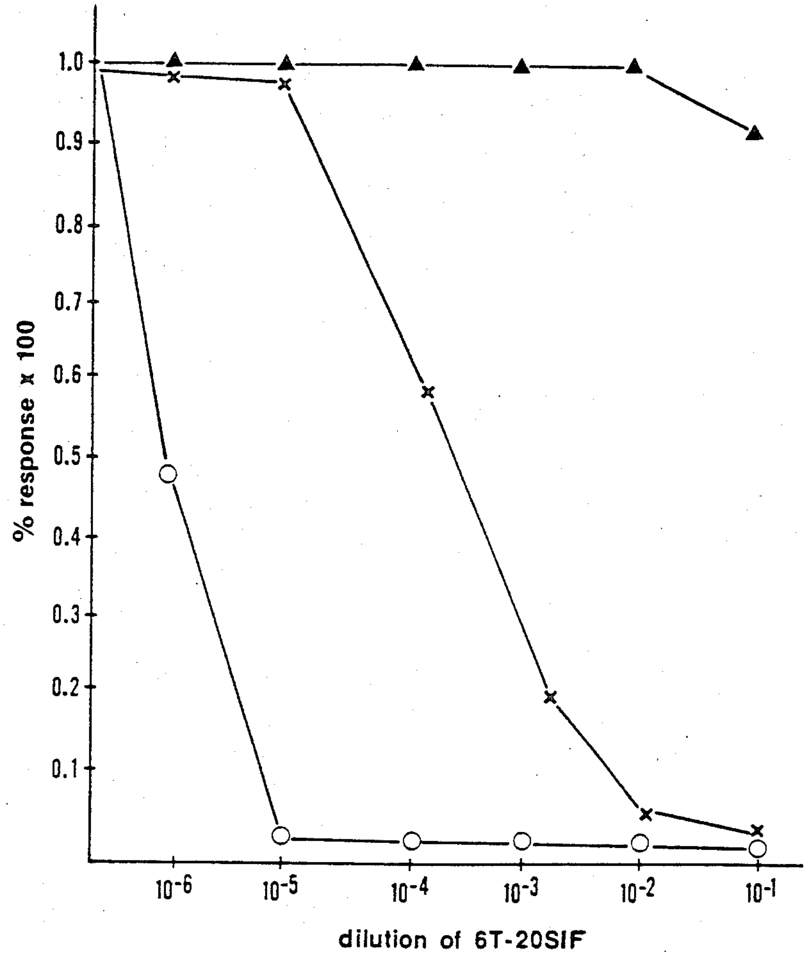
FIG. 3. Suppressive effect of 6T-20SIF on B cell proliferation. $10^5$ B cell (Δ), $10^5$B+$2\times10^4$T (×) or $10^5$T (o) were stimulated with 1/6 dilution of pokeweed mitogen (PWM) in the presence of various concentrations of 6T-20SIF. Proliferation was scored on day 4 by measuring $^3$H-thymidine uptake. The $^3$H-thymidine uptake for respective populations alone in PWM were 721±128 cpm, 17558±1216 cpm, and 41720±1910 cpm.

Effect of 6T-20SIF on B cell proliferation (FIG. 3).

The suppressive effect of 6T-20SIF on mitogen driven (PWM) B cell, T cell or B+T cell proliferation was studied. 6T-20SIF suppressed B cell proliferation only at $10^{-1}$ dilution, whereas almost 100% suppression of T cell proliferation was observed at $10^{-5}$ dilution. T cell dependent B cell proliferation was partially suppressed by 6T-20SIF at $10^{-4}$ dilution. Similar results were obtained in two other experiments. 6T-20SIF did not suppress PWM induced Ig synthesis at $10^{-1}$ dilution.

Figure 4:
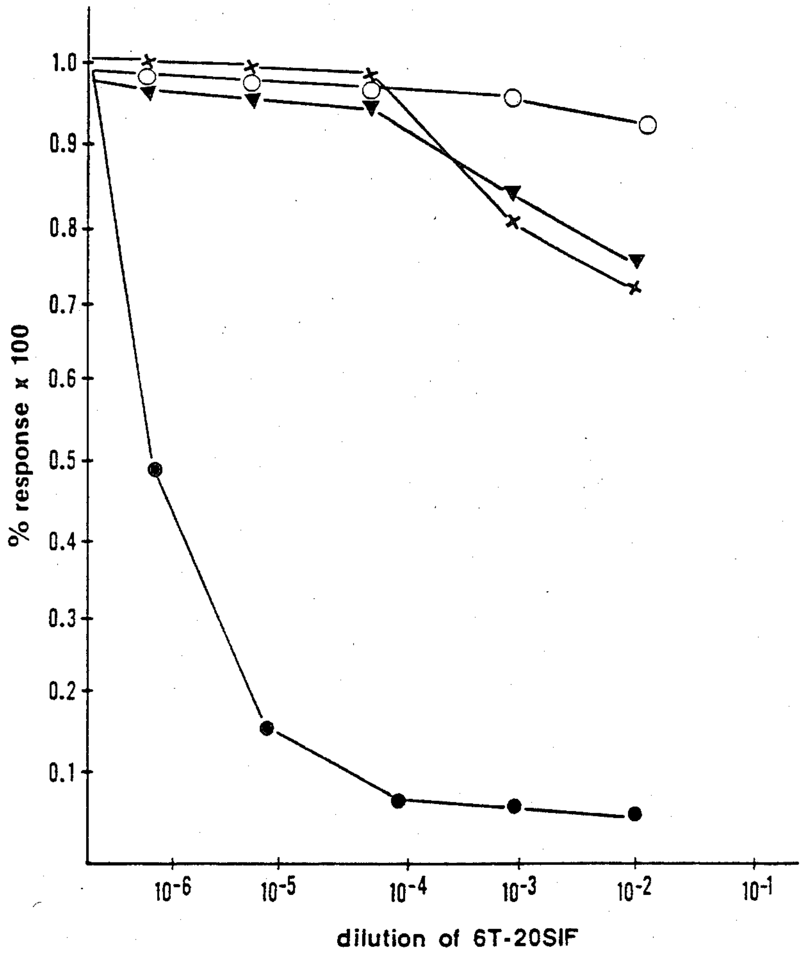
FIG. 4. Time course of 6T-20SIF induced suppression. $10^5$T cells were cultured with 0.1% of PHA in the presence of various dilutions of 6T-20SIF added at the initiation of culture period (●), 24 hours (×) or 48 hours later (o). $^3$H-thymidine uptake was measured 4 days later. $^3$H-thymidine uptake was also measured 3 days after culture initiation with 6T-20SIF added at the beginning of the culture period (Δ). The $^3$H-thymidine uptake for T cell alone in the presence of PHA in a 3 day culture was 16201±520 cpm and in a 4-day culture it was 19811±300 cpm.
Figure 5:
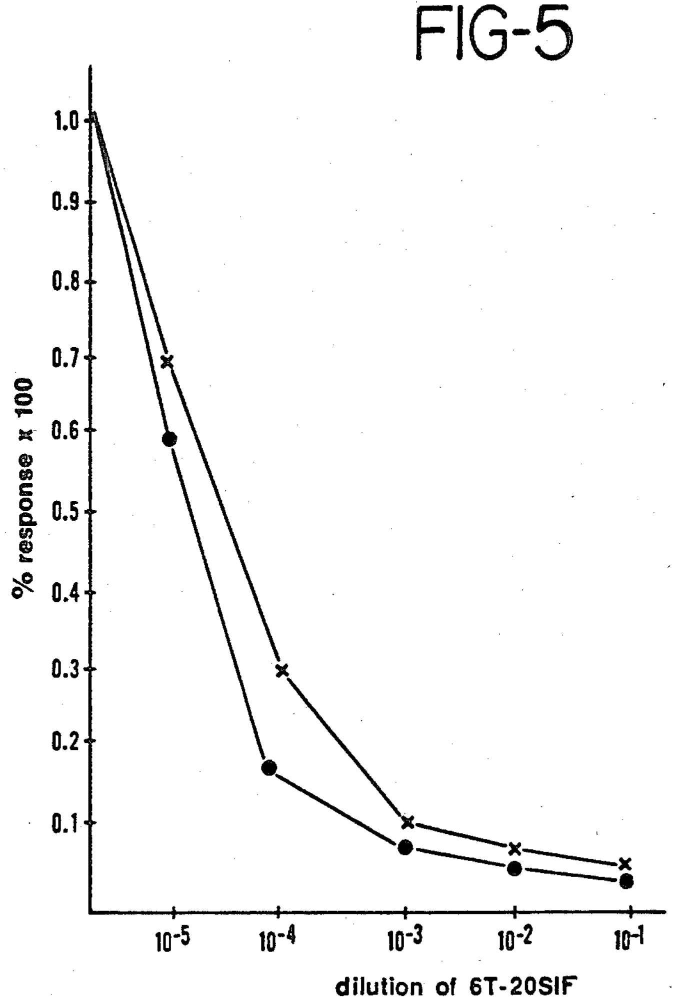
FIG. 5. Effect of different exposure times of T lymphocytes to 6T-20SIF on their responses to PHA-induced proliferation. T lymphocytes at $10^7$ cells/ml were exposed to various dilutions of 6T-20SIF as indicated for 8 hours (×) or 24 hours (●). Cells were washed extensively before set-up for PHA induced proliferation. $^3$H-thymidine uptake was measured 4 days later.

Time course of 6T-20SIF induced suppression (FIGS. 4,5).

In contrast to the marked suppression observed when 6T-20SIF was added at the initiation of the culture period, the suppressive effect of the same cell-free supernatant was reduced drastically when added 24 hours later. No suppressive effect was observed when 6T-20SIF was added 48 hours after culture initiation. In order to obtain maximum suppression, it is important that the minimum culture period be 4 days. If $^3$H thymidine uptake was measured 3 days instead of 4 days after culture initiation, with 6T-20SIF added at the beginning of the culture period, little suppression was observed.

Continuous presence of 6T-20SIF during the complete culture period is not required, however, to achieve maximum suppression. T lymphocytes were treated with medium or $10^{-5}$–$10^{-1}$ dilutions of 6T-20SIF at $10^7$ cells/ml for 8 to 24 hours at 37°. Cells were then washed 3–4 times and set up for PHA induced proliferation assay as described herein. As can be seen in FIG. 5, lymphocytes that were in contact with $10^{-3}$ dilution of 6T-20SIF for 8 hours or with $10^{-4}$ dilution of 6T-20SIF for 24 hours did not proliferate in response to PHA stimulation.

Figure 6:
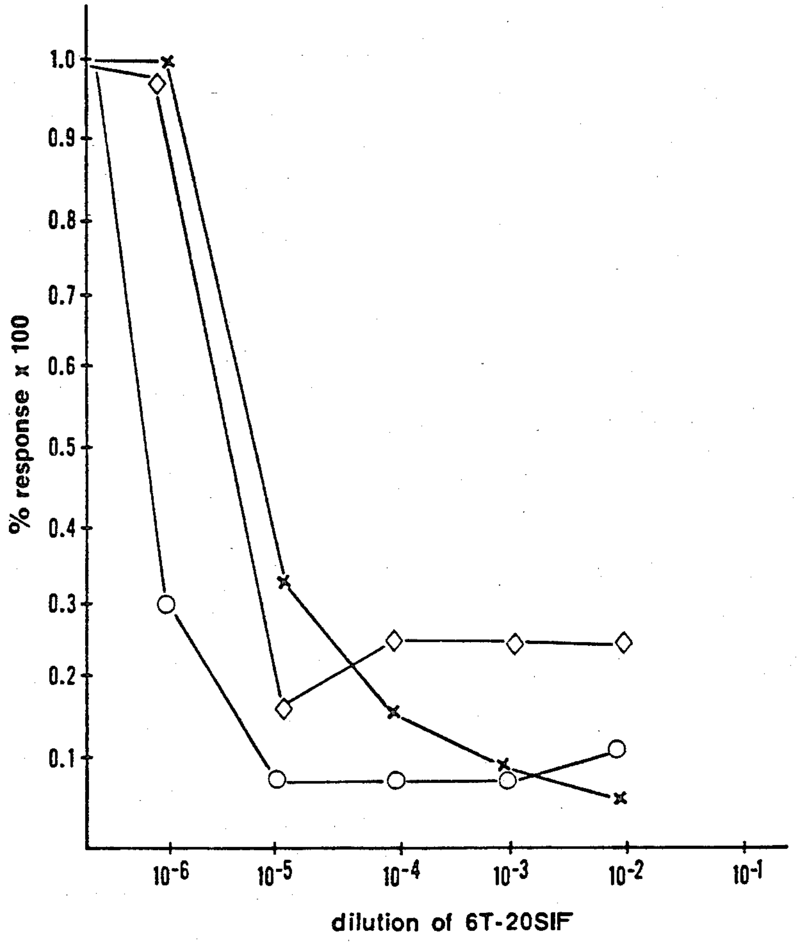
FIG. 6. Effect of 6T-20SIF on mixed lymphocyte culture (MLC). $10^5$ human T cells were stimulated with $10^5$ allogenic cells (×), $2\times10^5$ DBA mouse cells (o) or $10^5$ (Δ) autologous non-rosetted cells. All stimulator cells were treated with 30 μg mitomycin-C (mit-C) for 30 min. $^3$H thymidine uptake was measured 5 days later. The $^3$H-thymidine uptakes in the absence of 6T-20SIF were 13281±1927 cpm, 769±138 cpm, and 1234±107 cpm for the respective stimulation.
Figure 7:
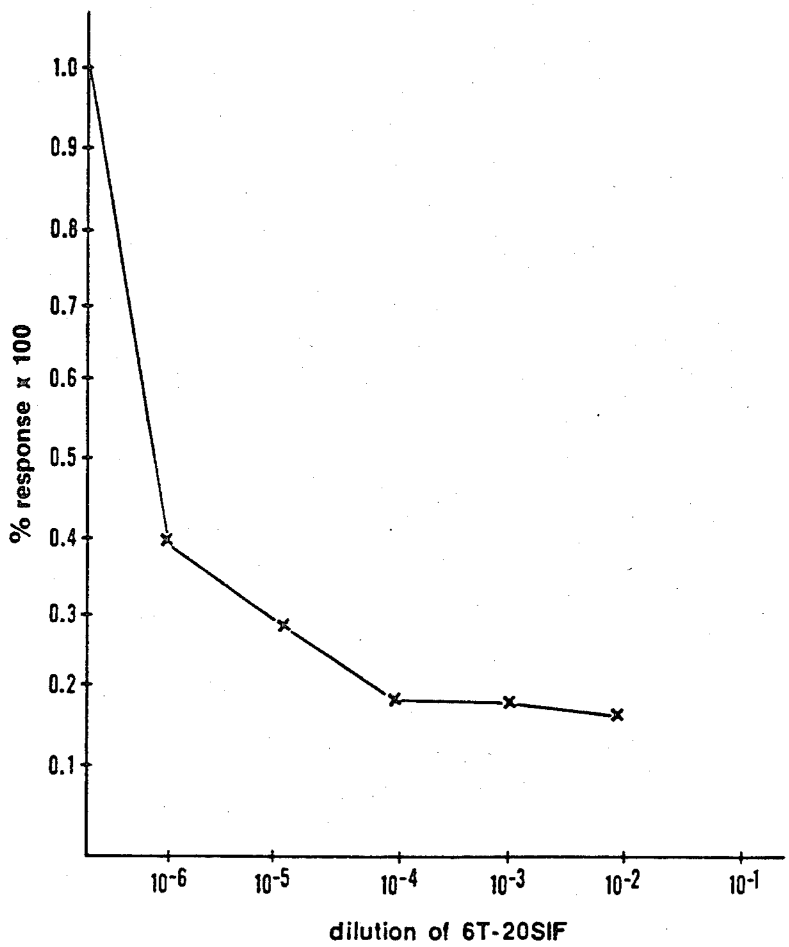
FIG. 7. Effect of 6T-20SIF on mouse spleen cells in an MLC assay. $2\times10^5$ C57/B6 cells were stimulated with $2\times10^5$ mit-C treated DBA cells (×). $^3$H-thymidine uptake was measured 5 days later. The $^3$H-thymidine in the absence of 6T-20SIF was 14161±141 cpm.

Effect of 6T-20SIF on one-way mixed lymphocyte cultures (FIGS. 6,7).

$10^5$ Human T cells were cultured with either $10^5$ allogenic non-rosetted cells, $2\times10^5$ DBA spleen cells, or $10^5$ autologous non-rosetted cells. Stimulated cells were treated with mit-C to arrest proliferation. As can be seen from FIG. 6, 6T-20SIF at dilution of $10^{-5}$ suppressed the proliferative response of T lymphocytes to stimulation by alloantigen, xenoantigen and autoantigen.

6T-20SIF was also tested in a mouse spleen cell mixed lymphocyte culture experiment. $2\times10^5$ C57/B6 spleen cells were cultured with various concentrations of 6T-20SIF in the presence of $2\times10^5$ mit-C treated DBA cells. The suppressive effect observed as shown in FIG. 7 was very similar to that of human lymphocytes. 6T-20SIF thus does not exhibit species restriction.

Figure 8:
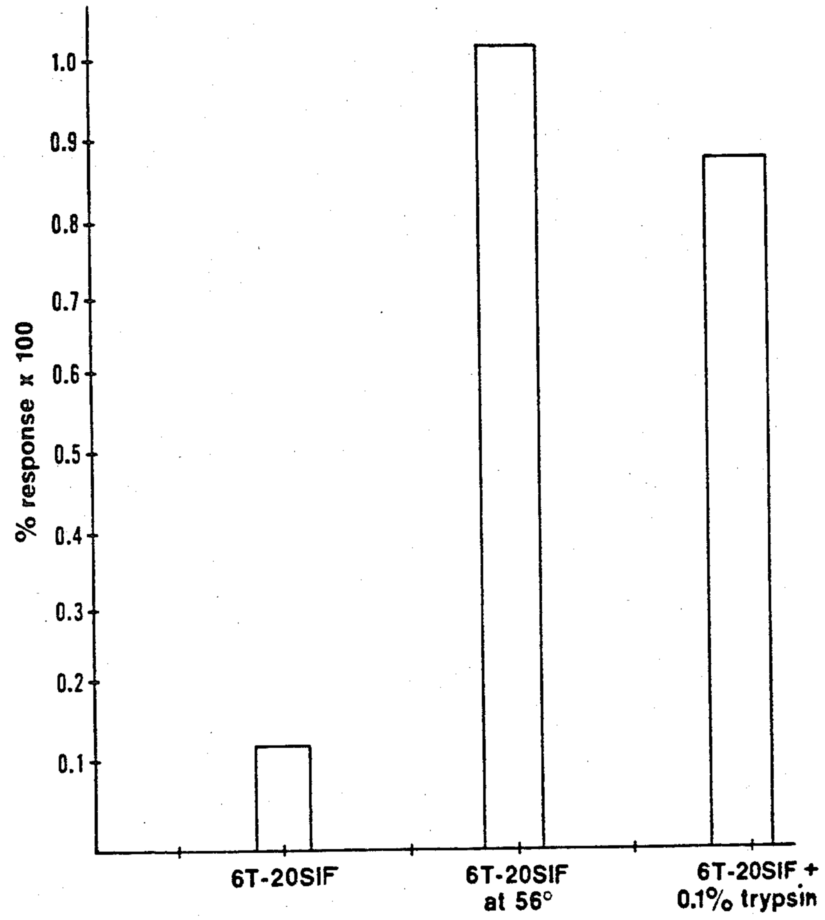
FIG. 8. Inhibition of the suppressive activity of 6T-20SIF by heat or trypsin treatment. 6T-20SIF was incubated at 56° for 30 min. or treated with 0.1% trypsin for 2 hours at 37°. The treated samples were then tested for their abilities to suppress PHA-induced T cell proliferation. The % response of PHA stimulated T cells in the presence of $10^{-1}$ dilution of the indicated samples are plotted.
Figure 9:
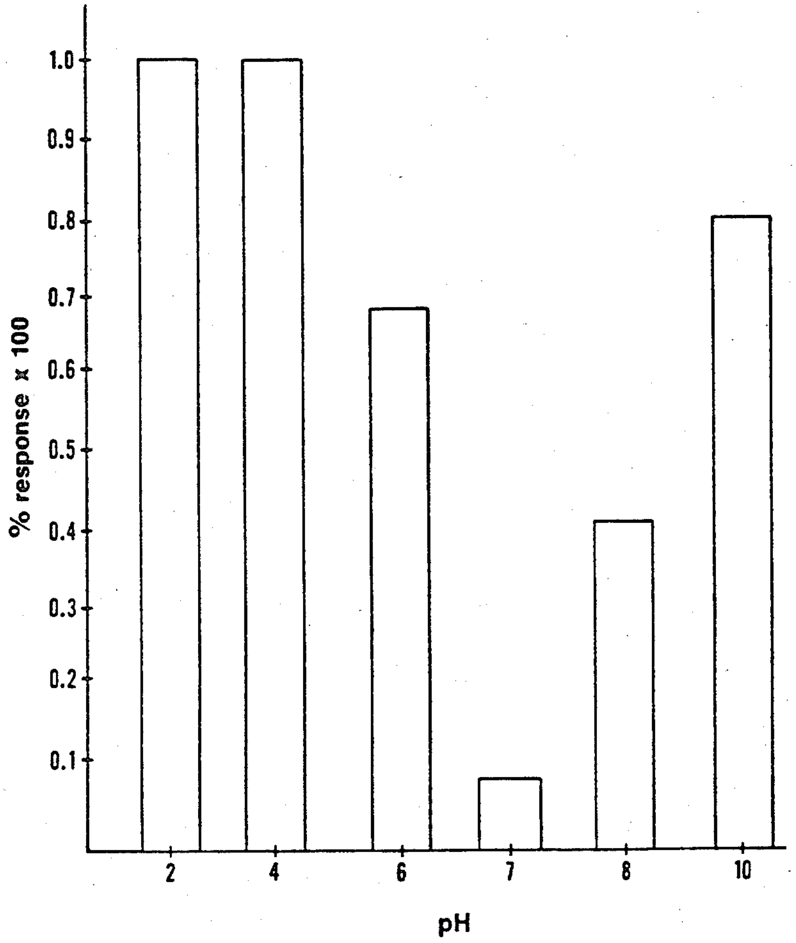
FIG. 9. Effect of different pHs on the activity of 6T-20SIF. 6T-20SIF was acidified or alkalized to various pHs, as indicated in the figure, for 30 minutes before being returned to neutral pH. Treated samples were then tested in the PHA induced T cell proliferation assay. The % response of PHA stimulated T cells in the presence of $10^{-2}$ dilution of various samples are plotted.

Effect of heat, acid, alkali and trypsin on the activity of 6T-20SIF (FIGS. 8,9).

As shown in FIG. 8, 2 hours incubation with trypsin removed about 90% of the activity of the factor. The factor is also sensitive to heat treatment, being inactivated by 30 minutes at 56° C. Titrating the supernatant to pH 2, 4, or 10 destroyed the activity completely, while the factor retained only 50% activity at pH 6 and pH 8.5. The factor seems to be most active at physiological pH (7.4) (FIG. 9).

Figure 10:
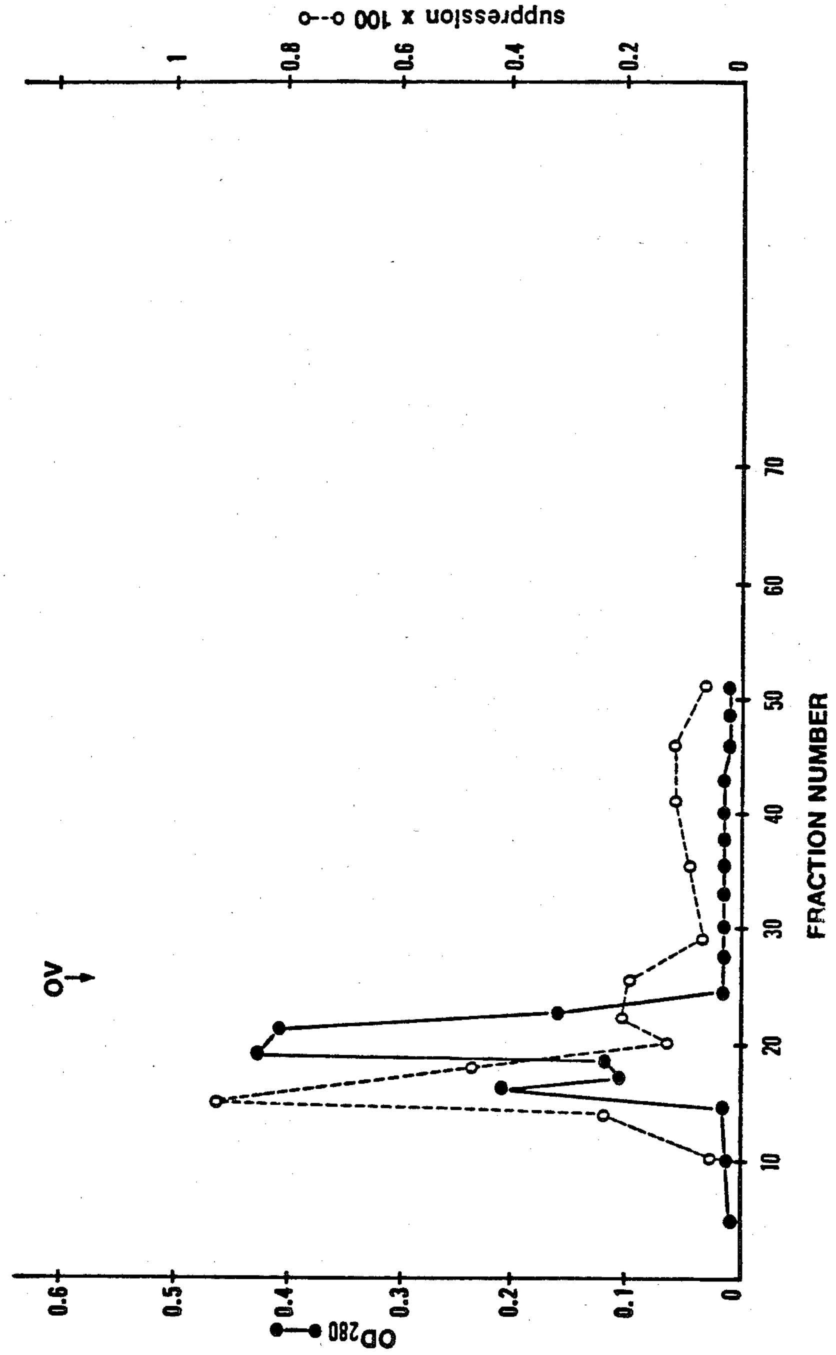
FIG. 10. Chromatography of 50% ammonium sulfate fraction on Sephacryl ® S-200 column. 2 ml of the 50% ammonium sulfate fraction of 6T-20SIF containing more than 90% of the suppressive activity was put on Sephacryl ® S-200 column. Both the optical densities (○---○) and suppressive effect on PHA induced T cell proliferation (●---●) were measured on alternate fractions as indicated on the graph. The % suppression is calculated according to the formula.

Sephacryl ®S-200 gel chromatography of 6T-20SIF (FIG. 10).

200 ml of cell free supernatant was fractionated by a ammonium sulfate precipitation. The 50% ammonium sulfate fraction containing 90–95% of the activity was put on a Sephracryl ®S-200 column. As can be seen in FIG. 10, most of the suppressor activity came out in the first protein peak, indicating that the MW of the factor is around 110,000 dalton.

Induction of suppressor cells by 6T-20SIF (FIGS. 11,12).

T lymphocytes were incubated at $3\times10^6$ cells/ml with different dilutions of 6T-20SIF or growth medium for 24 hours. Cells were washed extensively and then set up in coculture experiments with $5\times10^4$ fresh allogenic T cells in a PHA-induced proliferation assay or with $2.5\times10^4$ T cells and $10^5$ B cells in a PWM induced T cell dependent B cell proliferation assay. As can be seen in FIG. 11, T lymphocytes exposed to $10^{-4}$ dilution of 6T-20SIF for 24 hours suppressed 90–95% T cell proliferation in a coculture assay (suppression observed in 3 out of 3 experiments). T cell induced B cell proliferation was partially suppressed at around $10^{-2}$ dilution. The effect of 6T-20SIF treated T cells on fresh T cell proliferation in a one way mixed lymphocyte culture (MLC) stimulated by mit-C treated SB cells is shown in FIG. 12. 6T-20SIF pretreated T cells suppressed T cell proliferation in a one way MLC in a dose-related fashion with the pattern of suppression similar to the inhibition of mitogenic stimulation.

Production of suppressor factor by 6T-20SIF treated lymphocytes (FIG. 13, Table 5).

After 24 hours of exposure to 6T-20SIF or growth medium followed by extensive washing, T lymphocytes were set up at $1\times10^6$ cells/ml in RPMI+2% FCS. Supernatants were harvested at various times to test for suppressor activities in a PHA induced T cell proliferation assay. FIG. 13 depicts the results of this time-course experiment. Significant amounts of suppressor activity were released into the medium at 24 hours, whereas production of T cell suppressor factor (TSF) reached maximum level at around 48–72 hours (3 out of 3 experiments).

Production of TSF by different lymphoid populations and the effect of various treatments and culture conditions on the production are shown in Table 5. The purified T cell population is the major producer of TSF, while the depletion of residual adherent cells did not affect the amount of factor produced (2 out of 2 experiments). Both the OKT4+ population and the OKT8+ population are potent producers. A purified B cell population (less than 0.1% of T cells) produces about half of what purified T cells would have produced under the same culture condition (2 out of 2 experiments).

Production of TSF shows serum dependency. Serum-free medium did not support full production, whereas the presence of 2% FCS was sufficient for maximum secretion of TSF by T lymphocytes. Mit-C treatment and irradiation at 6000 R abolished almost completely the capacity of 6T-20SIF treated cells to elaborate TSF. Irradiation at 2000 R or 3000 R caused only partial abolition of TSF production.

Mechanism of action of TSF (FIG. 14, Table 6).

The suppressive effects of TSF on PHA induced T cell proliferation, PWM induced T cell dependent B cell proliferation, and PWM induced B cell proliferation are shown in FIG. 14. TSF suppressed 85–90% PHA induced T cell proliferation at around $10^{-3}$ dilution but showed only partial suppression on T cell dependent B cell proliferation at $10^{-2}$ dilution. Proliferation of PWM stimulated B lymphocytes was only slightly suppressed at $10^{-1}$ dilution (3 out of 3 experiments).

Thus, the pattern of suppressive activities is comparable to that of 6T-20SIF. Similar to 6T-20SIF, TSF has no suppressive effect on the generation of plaque-forming cells.

The effect of TSF on the generation of cytotoxic T cells is shown in Table 6. The generation of cytotoxic T cells against the B cell lymphoblastoid cell line SB was not affected by TSF at concentrations as high as $10^{-1}$ (2 out of 2 experiments).

The differential suppressive effects of TSF on various functional subsets of lymphocytes indicate that TSF suppresses via a noncytotoxic mechanism. This was further substantiated by studies showing that TSF did not augment the number of cells staining positively in the presence of trypan blue dye when cultured 3–5 days without mitogen (3 out of 3 experiments). Similar findings were also true for 6T-20SIF.

Time course of TSF-induced suppression (FIG. 15).

TSF was added to a PHA induced T cell proliferation assay at various times after culture initiation. When added at mid-culture period, suppressive activity was reduced by 50%, while no suppressive effect was observed when TSF was added at the last day of the culture period. The presence of TSF at the early phase of culture period is thus required for maximum suppression, which is similar to what was observed with 6T-20SIF. However, if TSF was added at the beginning of a culture period, there is little difference in percent suppression observed in a 3 or 4 day PHA-induced T cell proliferation assay. 6T-20SIF, on the other hand, did not show much suppressive effect on T cell proliferation in a 3 day lectin induced mitogenesis assay. A minimum of 4 day culture period is required for 6T-20SIF to exert maximum suppression.

Inhibition of the suppressive activities by monosaccharides and indomethacin (FIG. 16).

The suppressive effects of 6T-20SIF and TSF on PHA induced T cell proliferation were tested in the presence of 50 mM of each of α-methyl mannoside, fructose, NAG, or rhamnose, or 10 μg/ml of indomethacin. As shown in FIG. 16, of all the monosaccharides tested, only rhamnose blocked the suppressive activities of 6T-20SIF and TSF (2 out of 2 experiments). The prostaglandin synthetase inhibitor indomethacin has no effect on the suppressive activities of either; thus prostaglandin-like molecules do not seem to be involved in the mediation of suppression.

Inhibition of delayed-type hypersensitivity reaction by 6T-20SIF (FIG. 17).

The in vivo effect of 6T-20SIF was evaluated by measuring the inhibition of delayed type hypersensitivity in mice. On day zero, C3H male mice were immunized with 0.2 cc of a 0.01% solution of sheep red blood cells i.v. ($2\times10^5$ cells/mouse). On each of days 4 and 5, 50 μl of a 10% solution of 6T-20SIF was injected into the left foot pad of each mouse. As a control, 50 μl of saline was also injected into the right foot pad of each mouse on each of days 4 and 5. On day 5, the mice were challenged in each foot pad with 30 μl of a 20% solution of sheep red blood cells and foot pad measurements were made 24 hours later. As shown in FIG. 17, the delayed hypersensitivity reaction was significantly inhibited in mice receiving the 6T-20SIF. This example illustrates the in vivo utility of SIF to suppress undesired T cell proliferation.

The subject 6-thioguanine resistant mutant of the human lymphoblastoid cell line CEM secretes constitutively into the growth medium high titered immunosuppressive factor. The cell-free supernatant 6T-20SIF at dilutions as high as $10^{-9}$ suppressed at least 90% of T cell proliferation to both mitogenic and antigenic stimulations. T cell induced B cell proliferation was suppressed only by lower dilutions of the supernatant ($10^{-3}$) and mitogen stimulated B cell proliferation was only partially affected at dilutions of $10^{-1}$.

The parental line CEM also secretes into the growth medium low levels of previously uncharacterized suppressive factor. As shown by Vesole, et al., CEM supernatant caused a 50% inhibition in mitogenically-induced T cell proliferation at a dilution of $10^{-0.8}$. The parental CEM line used by Applicant was able to achieve the same degree of inhibition at a dilution of $5\times10^{-3}$, although this fact was not previously known. By contrast, the subject mutant cell line and its most productive subclones are capable of showing this same degree of inhibition at dilutions of $10^{-6}$ and $10^{-9}$, respectively. This vast enhancement in SIF secretion by 6T-CEM and its subclones over the parental cell line induced by 6-thioguanine appears not to be linked to deficiency in the enzyme hypoxanthine guanine phosphoribosyl transferase (HGPRT) since azaguanine resistant CEM which is also deficient in HGPRT shows no enhancement in SIF production compared to the parental line CEM.

Based on the state of the art as represented by Vesole, et al., and Irigoyen, et al., it is most surprising that one could make such a 6T-sensitive mutant of CEM or any other cell line which would secrete such high titers of SIF.

As indicated previously, this vast enhancement in SIF production makes possible for the first time its purification and characterization.

The cell-free supernatant of 6T-CEM-20, 6T-20SIF, suppressed equally well the proliferation of both OKT4+ and OKT8+ populations to PHA stimulation. Allogenic, xenogenic and autologous stimulation of T lymphocytes by mit-C treated stimulated cells were suppressed in similar fashion as were mitogenic stimulation. 6T-20SIF did not exhibit species restriction since it also suppressed mouse spleen cell proliferation to both mitogenic and allogenic stimulations.

In order to achieve maximum suppressive effects, 6T-20SIF is optimally present at the initiation of the culture period. No suppressive effect was observed when 6T-20SIF was added 48 hours after culture initiation, indicating that 6T-20SIF is probably involved in suppressing the early stages of mitogen induced proliferation with little or no effect on the terminal stages. The continuous presence of 6T-20SIF throughout the culture period is not required, since cells that had been exposed for 8 to 24 hours to 6T-20SIF did not respond to PHA induced proliferation. This cannot be caused by the presence of residual 6T-20SIF, since the medium from the last wash contained no suppressive activity. 6T-20SIF suppressed more profoundly PHA induced T cell proliferation in a 4-day culture than a 3-day culture, although the degree of PHA induced proliferation in the absence of 6T-20SIF did not show significant differences between the two culture periods. These findings suggest that 6T-20SIF induces lymphocytes to secrete a second factor which is responsible for mediating the suppression observed.

Partial purification by Sephacryl® S-200 gel chromatography indicates that 6T-20SIF is a high molecular weight protein of around 110,000 dalton. The activity and optical density profile did not change in the presence of mercaptoethanol or 0.1M salt. SDS gel electrophoresis of the active fraction showed a major band of protein around 110,000 dalton.

The subject 6-thioguanine resistant mutant of CEM secretes constitutively into its growth medium a suppressor inducer factor which induces human PBL to produce a T cell specific suppressor factor (TSF). Neither factor exerts its suppressive effect by a cytotoxic mechanism since there were no differences in cell viability between suppressed and control cultures 3 to 5 days after incubation. By contrast, the prior art suppressor agent cyclosporin is highly toxic.

The potent suppressive effect of 6T-20SIF on T cell proliferation is believed to be mediated via the induction of the lymphocyte specific TSF because: (1) The targets of action are identical for the two factors. Both 6T-20SIF and TSF suppressed 90–95% T cell proliferation to mitogenic and antigenic stimulation at high dilutions of $10^{-9}$ and $10^{-3}$ respectively. T cell dependent B cell proliferation to mitogen was partially suppressed by both at lower dilutions of $10^{-4}$ and $10^{-2}$. Mitogenic induced B cell proliferation and B cell differentiation were not suppressed by either; (2) The time course of suppression indicates that TSF and not 6T-20SIF is the immediate suppressor factor. When added at the time of culture initiation, TSF suppressed equally well T cell proliferation to PHA induced stimulation in a 3 or 4 day culture, whereas 6T-20SIF showed only partial suppression in a 3 day culture under the same conditions and maximum suppression was only observed in a 4 day culture. This observation can be explained by the fact that 6T-20SIF had to induce the elaboration of TSF from the lymphocytes which then mediated the appropriate suppression, resulting in a short lag period between culture initiation and the onset of suppression. Therefore, a minimum culture period of 4 days is required by 6T-20SIF for maximum suppression. As for TSF, direct suppression was exerted on lymphocytes at the initiation of the culture period and maximum suppression could be detected 72 hours later, the time when PHA induced T cell proliferation almost reached its maximum level (under the culture conditions herein PHA induced proliferation usually peaked at day 4); 3) The suppressive activities of both 6T-20SIF and TSF were blocked by the monosaccharide rhamnose but not by other monosaccharides such as fructose, NAG, or α-methyl mannoside or by the prostaglandin inhibitor indomethacin. Since the presence of rhamnose did not affect the level of 6T-20SIF induced TSF production, it is unlikely that rhamnose blocked the lymphocyte suppressive activity of 6T-20SIF by interfering with its ability to induce TSF. Therefore, the target for rhamnose-mediated blockage is TSF.

It is unlikely that the TSF activity detected was due merely to residual 6T-20SIF that was bound loosely onto the lymphocyte surface and was then gradually released into the supernatant during the subsequent culture period, since lymphocytes that were treated with 30 μg/ml of mit-C after exposure to 6T-20SIF did not elaborate TSF into the growth medium. Lymphocytes that were irradiated at 2000–3000 R showed partial loss of TSF producing capabilities whereas 6000 R irradiation abrogated TSF production completely. It appears that active cellular metabolism is required for TSF synthesis.

It is noteworthy that TSF suppressed 90% of T cell proliferation with little or no effect on the generation of cytotoxic T cells or T cell dependent Ig synthesis. This can be explained by the hypothesis that TSF suppressed mainly the rapidly proliferating population triggered by mitogenic or allogenic stimulation without affecting the functional activities of all the subsets. Studies with monoclonal antibodies indicate that while both OKT4+ and OKT8+ populations respond equally well to allogenic and mitogenic stimulations, only a subset within the OKT8+ population would become cytotoxic effector cells upon stimulation by class I MHC antigens (22). Reinherz, et al., (23) and Thomas, et al., (24) also demonstrated that only a minor subset within the OKT4 population is responsible for providing helper activity to B cells to produce Ig. It is likely that the functional properties of these particular subsets were not affected by TSF.

It appears that TSF inhibits synthesis of interleukin-2 (IL-2) receptors in suppressed mouse T cells but does not inhibit IL-2 production. This observation may explain the results described herein.

The functional characteristics of TSF distinguish it quite clearly from other soluble factors produced by lymphocytes during Concanavalin A (con A) or PWM stimulation (24–27). Firstly, it suppresses predominantly T cell proliferation with little or no effect of B cell proliferation or Ig secretion. Secondly, it suppresses T cell proliferation in an MLC assay but does not affect the generation of cytotoxic T cells in the same experiment. Thirdly, the concentration of TSF required to produce maximum suppression on T cell proliferation is much lower than other soluble factors described so far ($10^{-3}$ as compared to ½ or 1/10 dilutions).

Most of the known immunosuppressive factors secreted by human T cells suppress B cell differentiation. Groillot-Courvalin, et al., (15) recently constructed a human T—T hybridoma secreting a suppressor factor which suppressed PWM induced B cell differentiation but did not inhibit PWM induced T or B cell mitogenesis. Fleisher, et al., (28) also reported the production of immune suppressor supernate of B cells (SISS-B) that suppressed Ig production with no suppressive effects on cell-mediated immune response, i.e., MLC and the generation of cytotoxic T cells. These data suggest that T cell derived B cell specific suppressor factors are distinct molecules from T cell specific suppressor factor.

Two of the more well characterized lymphocyte derived suppressor factors of T cell proliferation are human soluble suppressor of T cell proliferation (SISS-T) (25) and lipid suppressor substance (LSS) (29). SISS-T was secreted by PBL upon activation by concanavalin A (Con A), had a MW of 30–45,000 dalton and suppressed mitogenic and antigenic stimulated T cell proliferation at around 1/10 dilution. SISS-T had little effect on B cell proliferation and differentiation. The suppressive activity of SISS-T was blocked by the monosaccharide NAG but not by rhamnose, α-methyl mannoside, or frucose. SISS-T was partially inactivated at 56° but stable during prolonged exposure to acid or base. LSS was secreted constitutively by an uncloned human cell line established from a cutaneous T cell lymphoma (29) and was active at 1/1000 dilution. A similar material was secreted by antigen-activated conventional cultures of human T cells, which was active at 1/10 dilution. It appears that TSF is dissimilar to SISS-T since TSF is not stable in prolonged exposure to acid or base and has a much larger molecular weight. TSF suppressed 90–95% T cell proliferation at $10^{-3}$ dilution whereas SISS-T inhibited 40–70% T cell proliferation at $10^{-1}$ dilution. Furthermore, since the suppressive activity of TSF is blocked by rhamnose and not NAG, TSF and SSIS-T are probably binding to different receptors on T cell surface. LSS is a lipid like substance extracted from serum or growth medium by ethanol. We know from our preliminary purification study that TSF is a protein or glycoprotein-like molecule which precipitated out in the 50% ammonium sulfate fraction. 6T-20SIF is also different from the proliferation inhibitory factor (PIF) secreted by PHA activated lymphocytes (8,9). The activity of PIF is limited to the cells of the same species from which PIF is derived, whereas 6T-20SIF exhibits no species restriction. 6T-20SIF suppresses, with similar potency, both human PBL and mouse spleen cell proliferation to allogenic stimulation.

Supernatants from mitogen activated lymphocytes usually contain a spectrum of biologically active soluble mediators like migration inhibitory factor MIF (2,3), lymphotoxin (4,5) and interferon (10,30). The functional characteristics, the biochemical and biophysical properties preclude the possibility that TSF is identical to any of the molecules mentioned above. It should be noted that 6T-20SIF is the only non-mitogenic suppressor-inducer material known, in contrast to such prior art materials as PHA.

The functional characteristics, the biochemical and biophysical properties of TSF clearly distinguish it from other suppressor factors described in the literature. Thus, both 6T-20SF and TSF are unique factors. Information relating to the production of the subject mutant cell line and subclones, as well as their properties, are given in the following Tables.

TABLE 1

| 6-Thioguanine (μg/ml) | % Cell Viability[1] |
|---|---|
| 0.5 | 51 |
| 5 | 43 |
| 10 | 32 |
| 20 | 5 |
| 30 | 4 |

[1]CEM cells were exposed to various concentrations of 6T for 7 days and viability was assayed by dye exclusion.

TABLE 2

| Cell Lines | % Viability[1] | Suppressor[2] Activity |
|---|---|---|
| CEM | 100 | $5 \times 10^{-3}$ |
| 6T-CEM | 10 | $10^{-6}$ |
| 6T-CEM | | |
| 2 | 0 | $10^{-6}$ |
| 4 | 0 | $10^{-6}$ |
| 13 | 2 | $>10^{-6}$ |
| 14 | 4 | $10^{-6}$ |
| 17 | 2 | $>10^{-6}$ |
| 18 | 0 | $10^{-6}$ |
| 19 | 0 | $10^{-6}$ |

TABLE 2-continued

| Cell Lines | % Viability[1] | Suppressor[2] Activity |
|---|---|---|
| 20 | 1 | $10^{-9}$ |

[1]CEM, 6T-CEM and its subclones tested for their sensitivity to aminopterin treatment (0.005 μg to 0.5 μg/ml). The viabilities of various cell lines after 7 day exposure to 0.05 μg of aminopterin were shown.
[2]Suppressor effect on T-Cell proliferation was measured according to the method described in Example IV. The dilutions of various supernatants exhibiting 50% suppression was shown. The entry ">$10^{-6}$" means that 50% supression was attained at dilutions higher than $10^{-6}$.

TABLE 3

Functional characteristics of CEM, its HGPRT-mutants and the biological activities of their supernatants

| Cell Lines | Aminopterin[1] Sensitivity | Doubling[2] Time | Karotype[3] | T-Cell[4] Suppressor Activity | B-Cell[4] Suppressor Activity | MLC[5] Suppressor Activity | Effect on[6] the Generation of Cytotoxic T-Cels | Induction[7] of TSF |
|---|---|---|---|---|---|---|---|---|
| CEM | 98 | 20 | 45 ± 16 | $5 \times 10^{-3}$ | $<10^{-1}$ | $5 \times 10^{-3}$ | 2 | $10^{-1}$ |
| 6T-CEM | 10 | 24 | 72 ± 12 | $10^{-6}$ | $<10^{-1}$ | $5 \times 10^{-5}$ | 2 | $10^{-3}$ |
| 6T-CEM-20 | 2 | 20 | 74 ± 14 | $>10^{-6}$ | $10^{-1}$ | $10^{-6}$ | 4 | $2 \times 10^{-4}$ |
| Az-CEM | 3 | 26 | 70 ± 18 | $<10^{-1}$ | $<10^{-1}$ | $<10^{-1}$ | 2 | $<10^{-1}$ |

[1]% viability of the cells after 7 days exposure at 0.05 μg/ml of aminopterin.
[2]Time required for the cells to double the number from a starting concentration of $5 \times 10^5$ cells/ml.
[3]Chromosomes from 100 cells were counted, means and standard deviations were shown.
[4]Suppressor activity on T-Cell and B-Cell proliferation was measured according to the method described in Example IV. See footnote b to Table 2 for details. The entry "$<10^{-1}$" means that lower than $10^{-1}$ dilution isrequired to attain 50% suppression of B cell proliferation. The entry "$>10^{-6}$" means that 50% suppression was attained at dilutions higher than $10^{-6}$.
[5]Suppressor activity on allogenic MLC was measured according to the method described in Example V. Dilutions of supernatant showing 50% suppression were shown. The entry "$<10^{-1}$" means that lower than $10^{-}$ dilution is required to attain 50% suppression of MLC reaction.
[6]Effect on the generation of cytotoxic T-Cell was measured according to method described in Example VII. Differences in % cytotoxicity between supernatant (used at $10^{-1}$ dilution) treated cells and medium treated cells were shown.
[7]Induction of TSF was measured according to the method described in Example II. Dilutions of TSF induced by the various supernatants that showed 50% suppression of T cell proliferation were shown.

TABLE 4

STABILITY DATA FOR 6T-CEM-20

| Period[1] | Suppressive Activity[2] |
|---|---|
| Jul. 82-Sept. 82 | $10^{-7}$ |
| Oct. 82-Dec. 82 | $5 \times 10^{-6}$ |
| Jan. 83-Mar. 83 | $10^{-7}$ |

[1]Suppressive supernatants were prepared from 6T-CEM-20 according to the method described in Example II.
[2]Suppressive activity on T-Cell proliferation was measured according to the method described in Example IV.

TABLE 5

Production of TSF by different populations of lymphoid cells and the effect of various culture conditions on the production

| | % PHA response* |
|---|---|
| A. Production of TSF by different lymphoid populations[1] | |
| PBL | 22 |
| T lymphocyte | 16 |
| T lymphocyte with adherent cell removed | 17 |
| B lymphocyte | 50 |
| OKT4+ T lymphocyte | 16 |
| OKT8+ T lymphocyte | 15 |
| B. Serum dependency[2] | |
| T lymphocytes in 10% FCS | 15 |
| T lymphocytes in 2% FCS | 16 |
| T lymphocytes in serum free medium | 80 |
| C. Sensitivity of TSF producing cells to mit-C and irradiation[3] | |
| Mit-C | 93 |
| 2000 R | 43 |
| 3000 R | 48 |

TABLE 5-continued

Production of TSF by different populations of lymphoid cells and the effect of various culture conditions on the production

| | % PHA response* |
|---|---|
| 6000 R | 72 |

*% response in a PHA induced T cell proliferation assay in the presence of $10^{-3}$ dilution of TSF. The 3H thymidine uptake for T lymphocytes alone in the presence of PHA is 13201 ± 216 cpm.
[1]Different purified lymphoid populations were incubated at $3 \times 10^6$/ml for 24 hours with 1/500 dilution of 6T-20SF. Cells were washed extensively and then set up at $10^6$/ml. Supernatants were harvested 72 hours later.
[2]T-lymphocytes were treated for 24 hours with 1/500 dilution of 6T-20SF as described in (a) and set up at $10^6$/ml in the presence of different serum concentrations as is indicated in the Table.
[3]T-lymphocytes were treated for 24 hours with 1/500 dilution of 6T-20SF as described in (a) and then treated with 30 μg of mit-C for 30 minutes or irradiated at 2000 R and 6000 R before set up at $10^6$/ml for TSF production.

TABLE 6

| Dilution of TSF | % Cytotoxicity[1] |
|---|---|
| — | 69 |
| $10^{-3}$ | 67 |
| $10^{-2}$ | 66 |
| $5 \times 10^{-2}$ | 62 |
| $10^{-1}$ | 62 |

[1]$10^5$ T lymphocytes were cultured with $10^4$ mit-C treated SB cells for 3-5 days in the presence of various concentrations of TSF. $^{51}Cr$ labelled SB cells were used as targets for cytotoxicity. % cytotoxicity was calculated according to the formula given in Example VII (page 14).

EXAMPLE IX

Diagnosis of Rheumatoid Arthritis

In general, the response of lymphocytes from a patient has been previously used to diagnose various autoimmune diseases such as systemic lupus erythematosis, see G. M. Kammer et al. in the Journal of Immunology, Volume 130, page 1706 (1983); R. S. Krakauer et al. in Clinical Immunology And Immunopathology, Volume 14, page 327 (1979); and D. B. Kaufman, et al. in Clinical Immunology and Immunopathology, Volume 13, page 9 (1979).

The 6-thioguanine resistant mutant of the human lymphoblastoid cell line CEM secretes a high titered immunosuppressive factor referred to herein as SIF which suppresses via inducing human T lymphocytes to secrete a T cell suppressor factor TSF. This endogenous suppressor factor is probably, by far, more active than any T cell suppressor factor ever described in the literature. It is reasonable to expect that such an endogenous factor may play an important physiological role in regulating the immune response.

It has now been found that the SIF of the present invention may be used to accurately and precisely diagnose rheumatoid arthritis in humans. This can be done in a relatively simple, inexpensive and fast procedure as described below.

Protocol

The following protocol takes into account fluctuation in TSF production among normals by different age groups, day-to-day variability in responses to SIF among normal individuals and the consistency of the testing itself. In general, this protocol involves taking whole blood from the subject, isolating the mononuclear (white) cells and rosetting the mononuclear cells with sheep red blood cells (SRBC) to isolate the E+ (erythrocyte rosetting) cells and testing production of TSF by the E+ cells after induction with the SIF of the invention (the A test) and testing the response of an identical sample of E+ cells after incubation with both SIF and TSF (referred to as the B test). The B test is used to be certain that the particular patient being evaluated is not a "non-responder" to the patient's own TSF.

1. 40 ml of heparinized blood is spun down at 1500 g (1500 times normal gravity) for 10 minutes.

2. The buffy coat is removed and layered onto a Ficoll-Hypaque gradient (7 ml of buffy coat to 5 ml of Ficoll-Hypaque). The tubes are then spun at 1500 g for 30 minutes.

3. Mononuclear cells at the interface are removed and washed 3 times with phosphate buffer saline (PBS).

4. Washed mononuclear cells are suspended in RPMI 1640 medium and 10% fetal calf serum (FCS) at $5\times10^6$ per ml. 1 ml of 0.1% neuraminidase treated SRBC is added to 5 ml of mononuclear cells and the mixture is allowed to sit for about 20 minutes. The tube is spun at 1000 g for 20 minutes over a Ficoll-Hypaque gradient.

5. The non-rosetted cells (B lymphocytes and monocytes and adherent cells) will be at the interface and the rosetted cells (T lymphocytes) will be in the pellet together with the SRBC. T lymphocytes are then recovered from the pellet by lysing SRBC with ammonium chloride. The T lymphocytes are washed 3 times with PBS.

6. Washed T lymphocytes are divided into 2 parts, one for production of TSF by SIF induction (the A test) and one for testing the response of the lymphocytes to standard preparations of SIF or TSF (the B test).

7. The A test: For testing the production of TSF, $3\times10^6$ T lymphocytes are incubated with growth medium (RPMI and 10% FCS) or with $5\times10^{-2}$ dilution of the column purified SIF. The production of SIF is described in Example II of the present specification and the column purification of Fractogel is described below. 24 hours after incubation, the cells are washed 3 times with PBS and resuspended in RPMI 1640 and 10% FCS at $10^6$ cells per ml. The supernatants containing TSF are collected three days later and the TSF activities induced by SIF are tested in a PHA induced T cell proliferation assay as described in #9 below on the same day using normal donor's lymphocytes as responders.

Chromatography on Fractogel, TSK HW-55(F) column: The 50% ammonium sulfate cut containing the suppressor activity (SIF) is further purified on a Fractogel, TSK HW-55(F) column (2.5 cm$\times$50 cm). The column is equilibrated with $\alpha$-MEM and has a flow rate of 30 ml per hour. 2 ml of the dialyzed, 50% ammonium sulfate precipitated fraction is applied on the column. It is eluted with the buffer $\alpha$-MEM. 4 ml fractions are collected. The protein profile is followed by reading optical density at 280 nanometers and the suppressive activity is monitored using the PHA-induced T cell proliferation assay described below in #9.

8. The B test: For testing the response to standard preparations of SIF and TSF, T lymphocytes from patients are suspended at $10^6$ per ml in RPMI 1640 and 10% FCS and responses to SIF or TSF are tested in a PHA induced T cell proliferation assay as described in #9 below with the patients' T lymphocytes as responders.

9. PHA induced T cell proliferation: T lymphocytes are suspended at $10^6$ cells per ml in RPMI 1640 and 10% FCS. These T lymphocytes are obtained from normal individuals and have been prescreened for reproducible responses to TSF. 100 microliters of cells are put into each well of a U-bottom microtiter plate. Various dilutions of TSF (for the A test) and SIF or TSF (for the B test) are added to each well in 20 microliter volume. 80 microliters of 1/400 dilution of PHA-P (Wellcome) are added to each well. Plates are incubated for 4 days and $^3$H-thymidine is added 4–5 hours before cell harvesting by the Flow-cell harvester. Three replicates are set up for each dilution of TSF or SIF. In every assay, SIF and TSF of known activities are run simultaneously with unknown samples for standardization purposes.

10. Data Analysis: All samples are counted in an Intertechnique Scintillation Counter. Data is recorded on paper tapes which are processed by computer. The computer output shows the mean and standard deviation (SD) of $^3$H-thymidine uptake of the 3 replicates, and the % response is calculated according to the formula: % response=(cpm of TSF or SIF treated cultures/cpm of medium treated cultures)$\times$100. The % response is then plotted against the appropriate dilutions of TSF or SIF used for inducing the suppression and the best fit line will be drawn through the data points constituting the slope. The dilution of TSF or SIF suppressing the response by 50% is then calculated. The slope is considered to be equal to the formula: slope$=(Y_1-Y_2)/(X_1-X_2)$ wherein $Y_1$ is 100%, $X_1$ is 0, $Y_2$ is 50% and $X_2$ is the dilution giving 50% suppression.

11. 10 to 15 normal donors from each of the following age groups were tested: 20–40, 41–50 and 51–65. Selected normals will be tested every month to assess day to day variations in responses among normal individuals and the consistency of the assay.

Blood samples from 32 normal individuals and 6 individuals with rheumatoid arthritis were tested according to the above-described protocol. The results are shown in the following Table 7 and demonstrate that the TSF activity of patients with rheumatoid arthritis is significantly lower than that obtained from normals of a similar age group, i.e., median$=9\times10^{-2}$ as compared as to 8.5 to $9\times10^{-4}$. In general, the concentration of TSF necessary to produce a 50% suppression of T cell proliferation in this test for a patient with rheumatoid arthritis is at least tenfold higher than the concentration of TSF produced from a normal individual. Thus, the SIF produced according to the present invention has been shown to be useful in the diagnosis of rheumatoid arthritis.

In summary, this aspect of the present invention comprises a method of diagnosing rheumatoid arthritis in a human subject which comprises (i) treating T lymphocytes from the blood of the subject with a standard and effective T cell suppressor factor-inducing concentration of the suppressor inducer factor of the present invention, (ii) determining the activity of the produced T cell suppressor factor, and (iii) comparing the activity of the T cell suppressor factor found in step (ii) with control values of T cell suppressor activity induced by the supressor inducer factor of the present invention which controls are obtained from human normals and humans known to have rheumatoid arthritis.

TABLE 7

| | TSF ACTIVITY |
|---|---|
| NORMAL DONOR NO. | |
| 1 | $1.1 \times 10^{-4}$ |
| 2 | $5 \times 10^{-3}$ |
| 3 | $6 \times 10^{-4}$ $5 \times 10^{-4}$, $8 \times 10^{-4}$* |
| 4 | $9 \times 10^{-4}$, $2 \times 10^{-4}$ |
| 5 | $5.5 \times 10^{-4}$, $6.2 \times 10^{-4}$* |
| 6 | $7 \times 10^{-4}$ |
| 7 | $7.0 \times 10^{-4}$ |
| 8 | $1.2 \times 10^{-4}$ |
| 9 | $7 \times 10^{-3}$ |
| 10 | $8 \times 10^{-3}$ |
| 11 | $9 \times 10^{-3}$ |
| 12 | $6.5 \times 10^{-5}$ |
| 13 | $6.4 \times 10^{-4}$ |
| 14 | $7.9 \times 10^{-4}$ |
| 15 | $7.3 \times 10^{-4}$ |
| 16 | $6 \times 10^{-4}$ |
| 17 | $6.8 \times 10^{-4}$ |
| 18 | $7.5 \times 10^{-4}$ |
| Donors 1-18 are 21-40 years in age | |
| $n = 18$ | |
| median $= 7.0 \times 10^{-4}$ | |
| 19 | $8.3 \times 10^{-4}$ |
| 20 | $6 \times 10^{-3}$, $6.2 \times 10^{-3}$* |
| 21 | $5.5 \times 10^{-3}$ |
| 22 | $8.5 \times 10^{-4}$ |
| 23 | $8.1 \times 10^{-4}$ |
| 24 | $7.3 \times 10^{-3}$ |
| 25 | $7 \times 10^{-4}$ |
| Donors 19-25 are 41-50 years in age | |
| $n = 7$ | |
| median $= 8.3 \times 10^{-4}$ | |
| 26 | $8 \times 10^{-4}$, $10^{-3}$* |
| 27 | $8.4 \times 10^{-4}$, $8 \times 10^{-4}$* |
| 28 | $9 \times 10^{-4}$ |
| 29 | $7 \times 10^{-4}$ |
| 30 | $9 \times 10^{-4}$ |
| 31 | $7 \times 10^{-4}$ |
| 32 | $8 \times 10^{-2}$ |
| Donors 26-32 are 51-65 years in age | |
| $n = 7$ | |
| median $= 9 \times 10^{-4}$ | |
| RHEUMATOID ARTHRITIS DONOR NO. | |
| 1 | $>10^{-1}$ |
| 2 | $>10^{-1}$ |
| 3 | $>10^{-1}$ |
| 4 | $8 \times 10^{-2}$ |
| 5 | $6 \times 10^{-2}$ |
| 6 | $8 \times 10^{-2}$ |
| $n = 6$ | |
| median $= 9 \times 10^{-2}$ | |

*TSF Activities Tested more than once

EXAMPLE X

Transplantation With SIF

Transplantation of tissue from a donor animal to a host animal may involve two types of cell-mediated responses. The first is termed the graft-versus-host disease (GvHD), which has clinical implications especially in bone marrow transplantation, and the second is host-versus-graft disease (HvGD), allograft rejection or simply rejection which has important implications in the transplant of kidneys, livers and other soft tissues. The cellular basis for such transplant phenomenon is described in Chapter 4 of "The Cellular Basis of the Immune Response", second edition, by Edward S. Golub, Sinauer Associates, Sunderland, Mass. (1981). Both responses pose serious problems for the host recipient of the grafted tissue. References include R. Korngold et al in the J. Exp. Med. pages 1687-1698, volume 148 (December 1978), the article "Infectious Complications of Human Bone Marrow Transplantation" by D. J. Winston et al in Medicine, pages 1-31, Vol. 58, No. 1 (1979) and "Bone Marrow Transplantation" in the New England Journal of Medicine, pages 895-902, Vol. 292, No. 17 (1975). The suppressor inducer factor of the present invention may be used in vitro to treat a donor tissue, e.g., bone marrow, to decrease or eliminate GvHD in the recipient host and can also be used to reduce or eliminate allograft rejection, e.g., by in vivo administration.

1. Prevention of GvHD In Bone Marrow Transplantation (Immune Incompetent Host)

In bone marrow transplantation, bone marrow is withdrawn from a histocompatible donor (HLA-compatible or -identical and mixed lymphocyte culture matched) and implanted, e.g., injected intravenously, into the host. Usually, this involves use of bone marrow from a donor to a sibling host. The reason for the transplantation of bone marrow is either the presence in the host of malignant cells in the immune system, e.g., in acute lymphocytic leukemia, acute non-lymphocytic leukemia or chronic myelogenous leukemia, or congenital blood disease, e.g., aplastic anemia or severe combined immuno deficiency, and the therapy is replacement of the bone marrow stem cells with healthy cells from the donor. Thus, prior to transplant, the bone marrow is destroyed, usually by total-body irradiation. Maturation of the transplanted cells will gradually replace both the lymphoid and hemopoietic systems of the host. It has been found that immature stem cells, the precursors of lymphoid cells and red cells which are transplanted will not recognize the host tissues as foreign and will mature into functionally useful cells for the host. The problem comes about when mature T cells are carried along with the grafted bone marrow. Once in the host they proceed to attack the host as foreign causing GvDH. A method has not yet been devised for separating the desirable immature stem cells in the graft from the mature T cells. When the mature T cells in the graft from the donor are implanted in the host, the suppressor-type T cells are the first to be activated and this situation results in severe immunosuppression and possibly interference with the maturation of the desirable immature stem cells resulting in what is termed "Acute GvHD". Acute GvHD lasts for about one hundred days and can be treated by the administration of chemotherapeutic and immunomodulating agents such as methothrexate, heterologous, antithymocyte globulin, corticosteroids and cyclosporin A. These agents are selected for their inhibitory effect on functional T lymphocytes. However, such non-specific agents must be given for several months after the transplant and adverse side effects include hepatic and renal toxicity.

"Chronic GvHD" occurs about one hundred days after bone marrow transplantation and is thought to be caused by proliferation of mature helper T-lymphocytes from the donor. Such helper cells then attack the host and the host will exhibit symptoms similar to progressive systemic sclerosis, lupus or Sjögren's syndrome.

From the above description of acute and chronic GvHD, it can be seen that a primary goal in bone marrow transplant research is the destruction or separation of mature T cells from the donor from the desirable immature stem cells. Attempts have been made to treat the graft with monoclonal anti-T-cell antibodies including the monclonal antibodies known as OKT 3 and OKT 11 described in U.S. Pat. Nos. 4,361,549 and 4,364,937, respectively. The use of OKT 3 in bone marrow transplantation is described by A. H. Filipovich et al. in the article "Pretreatment of Donor Bone Marrow With Monoclonal Antibody OKT 3 for Prevention of Acute Graft-versus-Host Disease in Allogenic Histocompatible Bone-Marrow Transplantation" in The Lancet, pages 1266–1269, June 5, 1982. With OKT 3, it was confirmed that almost all immunocompetent T-lymphocytes in the bone marrow samples were coated with OKT 3 at the time of infusion. However, complement which is necessary to lyse the cells after being coated with OKT 3, could not be used since rabbit complement which would bind effectively is known to be toxic to human hemopoietic cells and would adversely affect the engraftment. As stated in the Lancet article, " . . . further modifications for bone-marrow pretreatment will be needed to achieve effective prophylaxis against acute GvHD in histocompatible bone-marrow transplantation".

Against the above background, it has been found that the suppressor inducer factor of the present invention effectively reduces the complications of transplantation of tissue into immunologically incompetent hosts. Thus, another aspect of the present invention is in the method for transplanting bone marrow from a donor mammal to a host mammal which comprises the steps of destroying the bone marrow of the host, e.g., by irradiating the host mammal withdrawing the bone marrow graft from the donor mammal and implanting, e.g., injecting, the graft tissue into the host, the improvement which comprises treating the graft tissue, e.g., in vitro, with the suppressor inducer factor of the invention. This method is particularly suited to the transplantation of bone marrow, e.g., in humans. This method is demonstrated by the following experimentation.

Materials and Methods

Mice: To demonstrate the efficacy of the suppressor inducer factor of the present invention in bone marrow transplantation, it is necessary to use as a model, a system wherein any significant number of mature T cells transplanted into the host would cause an acute GvHD reaction and wherein the genotype (haplotype) of the surviving host could be analyzed to determine whether the engraftment has taken place. A healthy surviving host with the genotype of the donor in the hemopoietic and lymphoid systems would indicate the success of the transplant since such could not be possible unless acute GvHD had been eliminated.

The H-2 complex is a linked series of genes in a small segment of chromosome 17 of the mouse. For the present experimentation, the offspring ($F_1$) from C57BL/6(H-$2^b$) and DBA/2(H-$2^d$) parents designated by the strain $B_6D_2F_1$ (H-$2^{b\text{-}d}$) was used as the host recipient. One of its parents (C57BL/6) was used as the donor. Mice were purchased from Jackson Laboratories of Bar Harbor, Maine and were 8–10 weeks old at the start of the experiment. The host mice were irradiated with $^{137}Cs$ at a dose of 102 rads per minute for a total dose of 950 rads.

Cell Suspension: Bone marrow suspensions were obtained by aspirating phosphate-buffered saline through the marrow cavities of femurs of donor mice. Cells were washed three times in RPMI and suspended in RPMI+10% fetal calf serum for treatment.

SIF: The dialyzed 50% ammonium sulfate fraction of the suppressor inducer factor of the present invention described in Example VIII was prepared. The control supernatant was a 50% ammonium sulfate fraction and was prepared from the Az-CEM line described in Table 3 above. The control supernatant showed no detectable suppressive effect on T cell proliferation.

Procedure: Bone marrow cells from the donor mouse were removed and suspended at $5\times10^6$ cells per ml of RPMI and incubated with the suppressor inducer factor or control supernatant in an amount of 1:300 v/v (SIF/cells) for twenty-four hours. The cells were then washed two times and $2.5\times10^7$ parental bone marrow cells were injected intravenously into the receipient through the tail vein. Sixty-five days after transplantation, the genotype (or haplotype) of the surviving mice was determined by the method described in "Humoral and Cell Mediated Immune Responses in Fully Allogenic Bone Marrow Chimera Mice" by F. G. Onoé in J. Exp. Med., page 115, volume 151 (1980).

The results obtained are shown in the following Table 8.

TABLE 8

| | Mouse # | SURVIVAL TIME POST TRANS-PLANTATION (DAYS) | GENOTYPE ON DAY 65 |
|---|---|---|---|
| Control Super- | 1 | 35 | — |
| natant Treated | 2 | 39 | — |
| Graft | 3 | 45 | — |
| | | mean = 39.6 ± 5 | |
| SIF Treated Graft | 4 | >60 | >95% H$2^b$ |
| | 5 | >60 | >95% H$2^b$ |
| | 6 | >60 | >95% H$2^b$ |
| | | mean = >60 | |

As can be seen in the above Table 8, all animals from the control group (n=3) died within 45 days whereas the group receiving bone marrow treated with SIF (n=3) survived beyond 60 days. Further, the weights of the SIF treated animals did not decrease after transplantation and their physical condition remained good throughout the entire study. In contrast, at 20 days posttransplantation, the control mice started to lose weight and appeared to be in poor physical condition. Use of the SIF in an amount of 1:10,000 v/v or less only reduced the T-cell proliferation by about 90%. However, use of the SIF in an amount of 1:1000 v/v or greater, e.g., 1:300 as above or 1:100 or 1:500, produced a decrease in T-cell proliferation of about 95% or more. Thus, the SIF is used in the present invention in bone marrow transplantation preferably in an amount of at least about 1:1000 v/v (SIF/cells).

2. Allograft Rejection (Immune Competent Host)

As previously described, grafting of tissue from a donor to an immune-competent host, e.g., kidney, heart, liver or lung transplantation, poses significant problems in that the immune system of the host attacks the graft. Immunosuppressive drugs may be toxic to the host and a need exists for a non-toxic immunosuppressive material which allows the host to gradually accept the graft without destroying it in the interim. A further aspect of the present invention is a method for transplanting tissue from a donor to a host mammal where the host is immunologically competent which comprises the steps of removing the tissue from the donor mammal and implanting the tissue in the host while suppressing the immunological response of the host with the administration of the suppressor inducer factor of the present invention. While the amount of the suppressor inducer factor of the present invention can be titrated by the attending physician, the amount utilized will generally be in the range of about 0.1 to 1.0 ml of the 50% ammonium sulfate precipitated suppressor inducer factor described in Example VIII above per kilogram of body weight of the host per day. Such an amount of suppressor inducer factor of the present invention would be administered starting about one day before the transplant and daily thereafter for about two weeks.

REFERENCES

1. Altman, A., and D. Katz. 1982. The biology of monoclonal lymphokines secreted by T cell lines and hybridomas. Advances in Immunology 33: 73.
2. Remold, H. G., A. B. Katz, E. Haber, and J. R. David. 1970. Studies of migration inhibitory factor (MIF): recovery of MIF activity after purification by gel filtration and disc electrophoresis. Cell. Immuno. 1: 133.
3. Rockling, R. E. 1973. Production of migration inhibitory factor by nondividing lymphocytes. J. Immunol. 110: 675.
4. Kolb, W. P., T. W. Williams, and G. A. Granger. 1971. Lymphocyte activation and lymphotoxin production. In In Vitro Methods in Cell-Mediated Immunity. Edited by B. R. Bloom and P. R. Glade. Academic Press, New York, P. 333.
5. Rosenau, W., and C. D. Tsoukas. 1976. Lymphotoxin: a review and analysis. Am. J. Pathol. 84: 580.
6. Lawrence, H. S. 1954. The transfer of generalized cutaneous hypersensitivity of delayed tuberculin type in man by means of constituents of disrupted leukocytes. J. Clin. Invest. 33: 951.
7. Visa, D., J. M. Goust, R. Moulias, L. K. Trejdosiewicz, A. Collard, and N. Muller-Berat. 1975. In vitro production of transfer factor by lymphoblastoid cell lines. Transplant Proc. 8: 329.
8. Han, T., J. L. Pauly, and J. Minowada. 1975. Disparity in the production of lymphocyte inhibitory factor by cultured human T and B lymphoblastoid cell lines. Clin. Exp. Immunol. 2: 73.
9. Badger, A. M., S. R. Cooperband, and J. A. Green. 1974. Studies on the mechanism of action of proliferation inhibitory factor (PIF). Cell. Immunol. 13: 335.
10. Wheelock, E. F. 1965. Interferon-like virus inhibitor induced in human leukocytes by phytohemagglutinin. Science 149: 310.
11. Wallen, W. C., J. H. Dean, and D. O. Lucas. 1973. Interferon and the cellular immune response: separation of interferon producing cells from DNA synthetic cells. Cell. Immunol. 6: 110.
12. Moller, G. 1980. Immunol. Rev. 54. Academic Press, New York.
13. Taniguchi, M., and J. F. A. P. Miller. 1978. Specific suppressor T cell hybridomas. Curr. Topics in Microbiol. and Immunol. 81: 212.
14. Greene, W. C., T. A. Fleischer, D. L. Nelson, and T. A. Waldman. 1982. Production of human suppressor T cell hybridomas. J. Immunol. 129: 1986.
15. Grillot-Courvalin, C., J. C. Brouet, R. Berger, and A. Bernheim. 1981. Establishment of a human T cell hybrid line with suppressive activity. Nature 292: 844.
16. DeFreitas, E. C., S. Vella, A. Linnenbach, C. Zmijeweski, H. Koprowski, and C. M. Croce. 1982. Antigenspecific human T-cell hybridomas with helper activity. Proc. Natl. Acad. Sci. USA 79: 6646.
17. Irigoyen, O., P. V. Rizzolo, Y. Thomas, L. Rogozenski, and L. Chess. 1981. Generation of functional human T cell hybrids. J. Exp. Med. 154: 1827.
18. Gillis, S., and J. Watson. 1980. Biochemical and biological characterization of lymphocyte regulatory molecules. V. Identification of an interleukin 2 producer human T cell line. J. Exp. Med. 52: 1709.
19. Farrar, J. J., J. Fuller-Farrar, P. L. Simon, M. L. Hilfiker, B. M. Stadler, and W. L. Farrar. 1980. Thymoma production of T cell growth factor (interleukin 2). J. Immunol. 125: 2555.
20. Vesole, D. H., J.-M. Goust, J. W. Fett, and H. H. Fudenberg. 1979. Simulators and inhibitors of lymphocyte DNA synthesis in supernatants from human lymphoid cell lines. J. Immunol. 123: 1322.
21. Lau, C., and G. Goldstein. 1981. OKT 3 induces suppressor cells for mixed lymphocyte and PHA mitogenic responses in human peripheral lymphocytes. Int. J. Immunopharmac. 3: 187.
22. Reinherz, E. L., P. C. Kung, G. Goldstein, and S. F. Schlossman. 1980. A monoclonal antibody reactive with the human cytotoxic/suppressor T cell subset previously defined by a heteroantiserum termed $TH_2$. J. Immunol. 124: 1301.
23. Reinherz, E. L., C. Morimoto, K. A. Fizgerald, R. E. Hussey, J. F. Daley, and S. F. Schlossman. 1982. Heterogeneity of human T4+ inducer T cells defined by a monoclonal antibody that delineates two functional subpopulations. J. Immunol. 128: 463.
24. Thomas, Y., J. Sosman, D. Irigoyen, S. M. Friedman, P. C. Kung, G. Goldstein, and L. Chess. 1980. Functional analysis of human T cell subsets defined by monoclonal antibodies. I. Collaborative T-T interactions in the immunoregulation of B cell differentiation. J. Immunol. 125: 2402.
25. Greene, W. C., T. A. Fleisher, and T. A. Waldmann. 1981. Soluble suppressor supernatants elaborated by concanavalin A-activated human mononuclear cells. J. Immunol. 126: 1185.
26. Williams, R. C., and S. J. Korsmeyer. 1978. Studies on human lymphocyte interactions with emphasis on a soluble suppressor activity. Clin. Immunol. Immunopath. 9: 335.
27. Kaufman, D. B., C. Carnaud, J-L. Stach, and J-F. ach. 1979. The suppressive effect of a supernate from concanavalin A-activated lymphocytes. Effects of concanavalin A lymphocytes and their supernates on cytotoxic and mixed lymphocyte reactions. Cell. Immunol. 47: 153.
28. Fleisher, T. A., W. C. Greene, R. M. Blaese, and T. A. Waldmann. 1981. Soluble suppressor supernatants elaborated by concanavalin A-activated human mononuclear cells. II. Characterization of a soluble suppressor of B cell immunoglobulin production. J. Immunol. 126: 1192.
29. Wolf, R. L., S. H. Pincus, E. Merler, and F. S. Rosen. 1981. A diffuse cutaneous lymphoma secreting a potent immunosuppressant. Clin. Immunol. Immunopathol. 18: 351.
30. Wallen, W. C., J. H. Dean, and D. O. Lucas. 1973. Interferon and the cellular immune response: separation of interferon producing cells from DNA synthetic cells. Cell. Immunol. 6: 110.

The subject mutant cell line 6T-CEM and its subclone 6T-CEM-20 were deposited at the American Type Culture Collection, 12301 Parklawn Drive, Rockville, MD 20852, on Apr. 26, 1983, and were given ATCC accession number CRL 8296 and CRL 8295, respectively.

The present invention has been exemplified by the description above with reference to the mutant cell line 6T-CEM and its subclone 6T-CEM-20, and the SIF produced by this subclone (6T-20SIF). It should nevertheless be understood that this description was provided for exemplary purposes only and not to limit the scope of the subject invention, which scope is described only in the appended claims.

What is claimed is:

1. The stable 6-thioguanine resistant mutant T lymphoblastoid cell line ATCC CRL 8296, which mutant secretes constitutively a high titer of a T-cell suppressor inducer factor which is:

(i) non-mitogenic;

(ii) non-cytotoxic;

(iii) inactivated by 30 minutes at 56° C.;

(iv) suppresses at least 90% of mitogen-induced T cell proliferation at a dilution of $10^{-6}$;

(v) does not suppress mitogen-induced B cell proliferation at a dilution of $10^{-6}$; and (vi) does not suppress pokeweed mitogen induced Ig synthesis by B cells at $10^{-1}$ dilution.

2. The mutant T lymphoblastoid cell line of claim 1, which has a karyotype of 72±12.

3. The mutant T lymphoblastoid cell line of claim 1, which is produced by a process which comprises treatment of the parent CEM with between 20 μg/ml and 30 μg/ml of 6-thioguanine for a period of time sufficient to kill at least 90% of the cells.

4. The mutant T lymphoblastoid cell line of claim 3, wherein said process further comprises isolation of the viable cells after said 6-thioguanine treatment.

5. The mutant T lymphoblastoid cell line of claim 4, wherein said process consists essentially of said treatment and isolation.

6. The mutant T lymphoblastoid cell line of claim 3, wherein said process consists essentially of said treatment.

7. The mutant T lymphoblastoid cell line of claim 3, wherein:

said parent CEM is to be treated is not sensitive to 0.05 μg/ml of aminopterin, and the mutant T cell line product of the treatment is sensitive to 0.05 μg/ml of aminopterin.

8. The mutant T lymphoblastoid cell line of claim 3, wherein said parent CEM to be treated has the properties of ATCC CRL 119.

9. The mutant T lymphoblastoid cell line of claim 1, which secretes a suppressor-inducer factor which suppresses the cell proliferation of both OKT4+ and OKT8+ T cell populations.

10. A stable subclone of the mutant T lymphoblastoid cell line of claim 1.

11. The subclone of claim 10, which secretes a suppressor-inducer factor which suppresses the cell proliferation of both OKT4+ and OKT8+ T cell populations.

12. The subclone of claim 10, which secretes a suppressor-inducer factor that suppresses at least 90% of mitogen induced T cell proliferation at a dilution of $10^{-9}$ but does not suppress mitogen-induced B cel proliferation at said dilution.

13. The subclone of claim 10, which has the properties of ATCC CRL 8295.

14. The mutant T lymphoblastoid cell line of claim 1, wherein the titer of said factor remains constant for at least 8 months.

15. The mutant T lymphoblastoid cell line of claim 1, wherein said suppressor inducer factor:

suppresses mouse spleen cell proliferation to mitogenic stimulation with the same potency as it suppresses human peripheral blood lymphocyte proliferation to mitogenic stimulation.

16. The mutant T lymphoblastoid cell line of claim 1, wherein said mitogen used for proliferation is phytohemagglutinin.

17. The mutant T lymphoblastoid cell line of claim 1, wherein said suppressor inducer factor is antigen nonspecific.

18. The mutant T lymphoblastoid cell line of claim 1, wherein said parent CEM has a cell viability of about 5% after exposure to 20 μg/ml of 6-thioguanine.

19. A human suppressor factor which is antigen nonspecific and which:

(a) at a dilution of up to $10^{-6}$ suppresses at least 90% of mitogen induced T cell proliferation;

(b) does not suppress mitogen-induced B cell proliferation at a dilution of up to $10^{-6}$;

(c) does not suppress pokeweed mitogen induced Ig synthesis by B cells at $10^{-1}$ dilution;

(d) is inactivated by 30 minutes at 56° C.;

(e) is contained in a high molecular weight protein of about 110,000 dalton;

(f) exhibits maximum suppressor activity at physiological pH;

(g) suppresses the proliferation of both OKT4+ and OKT8+ T cell populations;

(h) is non-mitogenic and non-cytotoxic; and (i) suppresses mouse spleen cell proliferation to mitogenic stimulation with the same potency as it suppresses human peripheral blood lymphocyte proliferation to mitogenic stimulation.

20. The suppressor inducer factor of claim 19, produced by 6T-CEM or a subclone of 6T-CEM.

21. The suppressor inducer factor of claim 19, wherein said physiological pH is between 6 and 8.5.

22. The suppressor inducer factor of claim 19, wherein said physiological pH is about 7.4.

23. The suppressor inducer factor of claim 19, wherein about 90% of the activity of the factor is lost after 2 hours incubation with trypsin.

24. The suppressor inducer factor of claim 19, wherein said mitogen is phytohemagglutinin.

* * * * *